(12) United States Patent
Bennett et al.

(10) Patent No.: US 9,649,128 B2
(45) Date of Patent: May 16, 2017

(54) ADJUSTABLE CURETTE

(71) Applicant: Novon Solutions, LLC, Waunakee, WI (US)

(72) Inventors: Joseph Bennett, Waunakee, WI (US); Mark Stauber, Palo Alto, CA (US)

(73) Assignee: Novon Solutions, LLC, Waunakee, WI (US)

( * ) Notice: Subject to any disclaimer, the term of this patent is extended or adjusted under 35 U.S.C. 154(b) by 17 days.

(21) Appl. No.: 14/590,880

(22) Filed: Jan. 6, 2015

(65) Prior Publication Data
US 2015/0157357 A1    Jun. 11, 2015

Related U.S. Application Data

(60) Provisional application No. 61/910,473, filed on Dec. 2, 2013.

(51) Int. Cl.
| | | |
|---|---|---|
| *A61B 17/3205* | (2006.01) | |
| *A61B 17/3207* | (2006.01) | |
| *A61B 17/54* | (2006.01) | |
| *A61B 18/08* | (2006.01) | |
| *A61B 17/32* | (2006.01) | |
| *A61B 17/00* | (2006.01) | |
| *A61B 18/14* | (2006.01) | |

(52) U.S. Cl.
CPC ...... *A61B 17/320708* (2013.01); *A61B 17/54* (2013.01); *A61B 18/082* (2013.01); *A61B 2017/00747* (2013.01); *A61B 2017/00761* (2013.01); *A61B 2017/320008* (2013.01); *A61B 2018/1407* (2013.01); *A61B 2018/1412* (2013.01)

(58) Field of Classification Search
CPC ....... A61B 2017/320004; A61B 2017/320008; A61B 17/3207; A61B 17/320708; A61B 18/082; A61B 17/54; A61B 2018/1412; A61B 2018/1407; A61B 2017/00761; A61B 2017/00747
See application file for complete search history.

(56) References Cited

U.S. PATENT DOCUMENTS

| | | | | |
|---|---|---|---|---|
| 651,395 | A * | 6/1900 | Stapp | A61B 17/32070 606/160 |
| 654,763 | A * | 7/1900 | Russell | A61B 17/32070 606/160 |
| 827,193 | A * | 7/1906 | Thrash | A61M 25/04 604/105 |
| 879,297 | A * | 2/1908 | Moormeister | A61B 17/32070 606/160 |
| 928,011 | A * | 7/1909 | Whitlock | A61B 17/32070 606/160 |

(Continued)

*Primary Examiner* — Ryan J Severson
(74) *Attorney, Agent, or Firm* — Bycer Law, PLC; Matthew L. Bycer

(57) ABSTRACT

An adjustable, disposable dermal curette is structured to allow a user-practitioner to ergonomically grip a handle and manipulate an adjustable slider with a digit of their hand in order to change the diameter size of the flexible blade formed in an adjustable loop to the useful range of diameter sizes required. The user-practitioner can lock and unlock the slider in place quickly without the need to interrupt their procedure. The adjustable curette solves the problem of requiring multiple curette loop sizes for a procedure and results in improved quality of care and a savings of time and healthcare dollars.

26 Claims, 17 Drawing Sheets

(56) References Cited

U.S. PATENT DOCUMENTS

| | | | | |
|---|---|---|---|---|
| 932,103 | A * | 8/1909 | Black | A61B 17/32070 606/160 |
| 1,092,914 | A * | 4/1914 | Jones | A61B 17/32070 606/160 |
| 1,155,169 | A * | 9/1915 | Starkweather | A61M 25/04 604/105 |
| 3,491,747 | A * | 1/1970 | Robinson | A61B 10/0291 600/570 |
| 3,502,082 | A * | 3/1970 | Chatfield | A61B 17/32070 30/40.1 |
| 3,635,222 | A * | 1/1972 | Robinson | A61B 17/32070 128/840 |
| 4,245,653 | A | 1/1981 | Weaver | |
| 4,890,611 | A * | 1/1990 | Monfort | A61B 17/221 600/587 |
| 5,613,973 | A * | 3/1997 | Jackson | A61B 17/0218 606/1 |
| 5,902,314 | A * | 5/1999 | Koch | A61B 17/50 606/160 |
| 6,074,405 | A * | 6/2000 | Koch | A61B 17/50 606/160 |
| 6,440,138 | B1 * | 8/2002 | Reiley et al. | 606/79 |
| 7,587,992 | B2 | 9/2009 | Dunn et al. | |
| 2004/0194729 | A1 * | 10/2004 | Dunn | A01K 13/002 119/631 |
| 2006/0074434 | A1 * | 4/2006 | Wenstrom | A61B 17/17 606/96 |
| 2007/0060933 | A1 * | 3/2007 | Sankaran | A61B 17/16 606/160 |
| 2008/0183199 | A1 * | 7/2008 | Attinger | A61F 9/00736 606/161 |

* cited by examiner

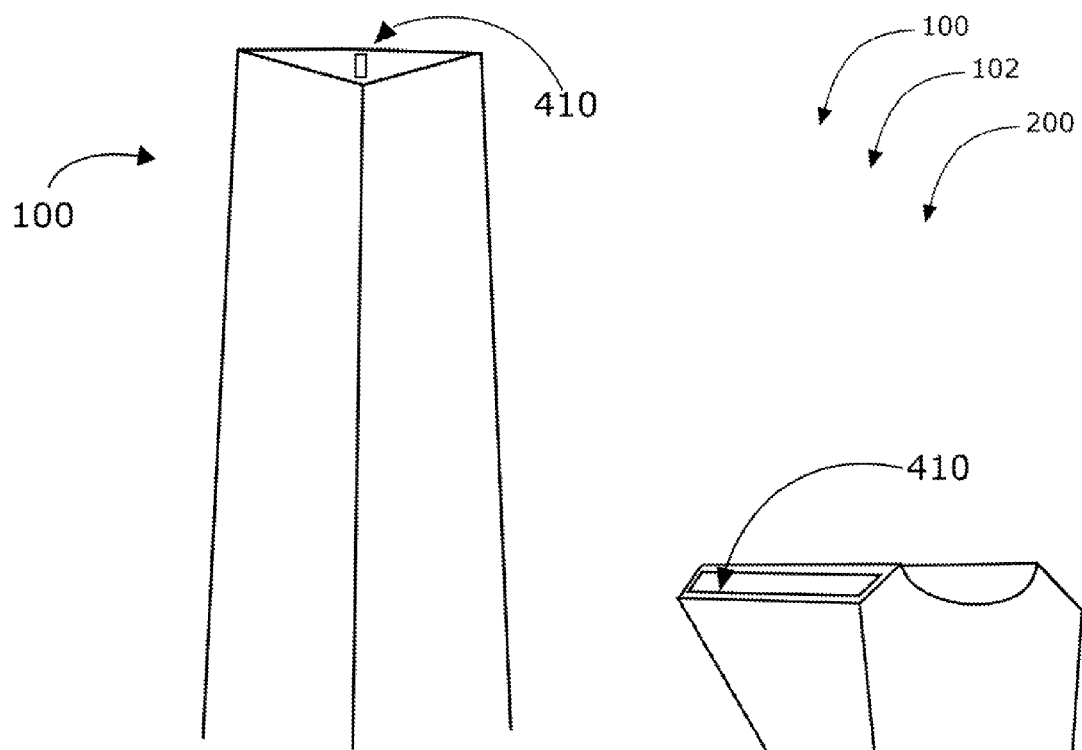

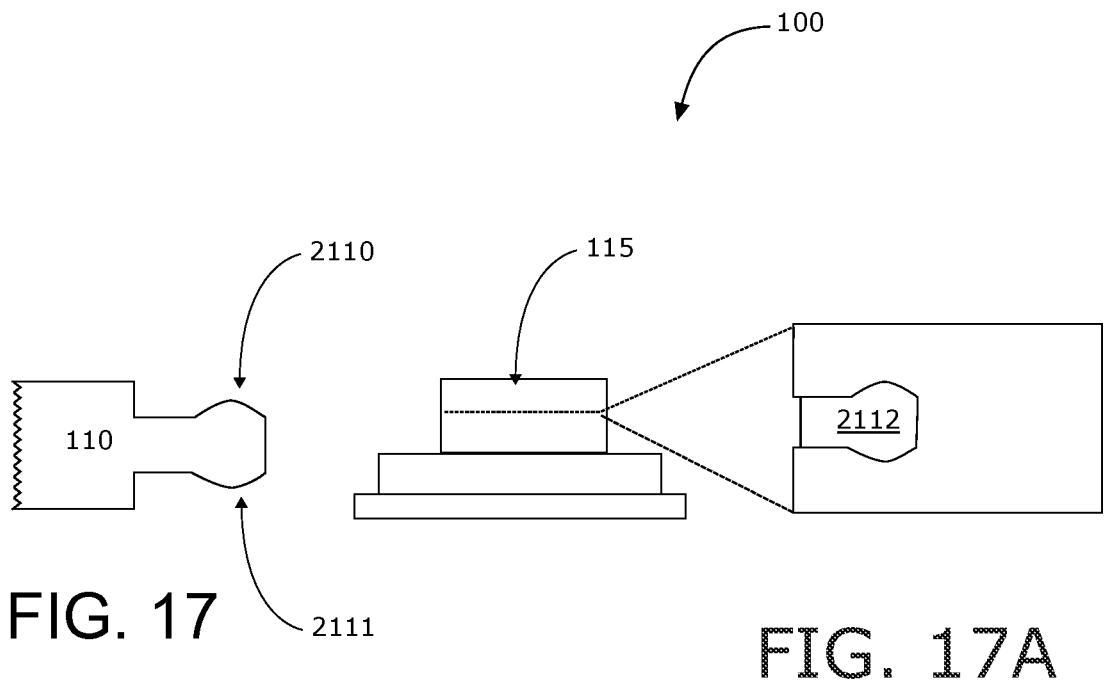
FIG. 17
FIG. 17A
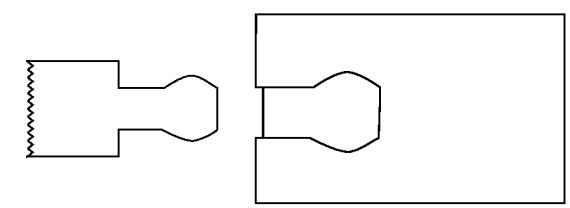
FIG. 17B
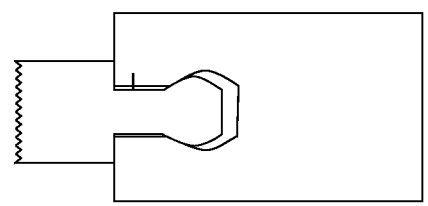
FIG. 17C

ADJUSTABLE CURETTE

CROSS-REFERENCE TO RELATED APPLICATION

The present application is related to and claims priority from prior provisional application Ser. No. 61/910,473, filed Dec. 2, 2013 which application is incorporated herein by reference.

BACKGROUND OF THE INVENTION

1. Field of the Invention

The present invention relates generally to the field of surgical instruments and more specifically relates to a manually adjustable and disposable dermal curette.

2. Description of the Related Art

This invention relates generally to medical devices for removing slough and devitalized tissue from a wound surface and edges, scraping skin lesions, and more particularly to an improved disposable dermal curette which can respond to the changes in blade diameter required to debride a wound thoroughly.

A dermal curette is a device used by medical practitioners for scraping and debriding devitalized tissue, biofilm, and slough from chronic wounds; as well as growths, such as skin cancers, warts, actinic keratosis and seborrheic keratosis, from the surface of the skin. Generally, such devices are simple in construction, with a handle and a working element having a sharpened edge, which is used to scrape the surface of the wound or skin and remove the targeted tissue or debris. The working element is commonly a circular or ring-like configuration providing a curved or circular sharpened edge as the working surface of the curette.

There are generally three basic types of dermal curettes: the Fox Curette, the Piffard curette, and the eye curette. The Fox curette is a device having a flat handle, usually metallic, with a generally cylindrical arm extending from the handle, also metallic, terminating in a working element having an oval or rounded-loop cutting edge. The Piffard Curette has a large metal handle tapering inwardly from the bottom of the handle, with a generally cylindrical metallic arm extending from the handle and terminating in a working element having an oval or rounded-loop cutting edge. The Piffard Curette is further provided with grooves or ribbed surfaces extending lengthwise along the handle of the curette. The eye curette is similar in design to the Fox Curette, but has a working element, which is dish-like rather than looped-shaped, resulting in a working edge with a scooping action. The eye curette also has grooves or ribbed surfaces, which extend around the width of the handle. Variations of the dermal curettes described above are available and are identified and marketed as the Buck, Skeele, or Heath curettes. These curettes, as well as the ones described above, are made to be reused multiple times, that is, designed and manufactured far repeated use after sterilization and, if necessary, resharpening.

Dermal, curettes of such designs have been, and are currently being, used by physicians and mid-level providers in medical procedures for the removal of devitalized tissue, slough, biofilm and debris in chronic wounds, as well as lesions and unhealthy growths from the surface of the skin of a patient. Generally, the removal of slough and biofilm is done without anesthesia. However, in some procedures, the physician anesthetizes the area, removes the lesion or greater amounts of tissue with a scraping action utilizing a dermal curette and then cauterizes or electrode-siccates the area scraped if hemostasis is not achieved through compression. Sometimes the procedure is reversed in part and, after anesthetizing the area, the lesion is desiccated and then scraped using a curette. Ideally, all of the slough, biofilm, devitalized tissue, lesions or unhealthy tissues or growths are removed in the scraping procedure with minimal destruction of the remaining healthy tissues. A body of clinical research has shown that a thorough and effectively defended wound is key to a fast and quality recovery.

As with many medical procedures, the effectiveness of such scraping procedures depends upon two interrelated factors, namely, the skill of the physician or mid-level provider and the design of the tool used.ABnormalities of the skin, such as slough, biofilm, debris, and devitalized tissue in a chronic wound; as well as cancers, warts, actinic keratosis and seborrheic keratosis, differ to the touch from healthy tissues. Therefore, the experienced provider relies on the sense of touch during the scraping procedure and "feels' the difference between healthy and unhealthy tissues. With the proper tools, the provider can use their sense of touch, to judge the depth of scraping necessary to remove only the targeted and unhealthy tissues, leaving the healthy tissues relatively unharmed.

Sharp debridement uses scalpels and curettes. Due to the complex structure of a chronic wound and the medical goal of achieving a thorough debridement, a typical debridement will require multiple sizes of curettes. Many procedures involve multiple wounds and new curettes are used for each wound. For practitioners, needing to switch back, and forth between multiple curettes for a wound is slow, cumbersome, and as a result leads to imprecise, ineffective debridements. For hospitals, multiple curette sizes represents unnecessary added costs, biohazardaus waste, and storage.

To accomplish this meticulous work in detail, a practitioner uses a variety of sizes. Based on feedback from one clinician, the max hoop size needed is 8 mm and the minimum hoop size is 2 mm. The range of sizes offered by a leading manufacturer of dermal curettes is 1 mm to 8 mm, with some only ranging 2 mm-7 mm.

Ideally, an adjustable curette should provide an ergonomic handle and a digitally-actuable means for selectively increasing and decreasing a diameter size of a blade formed into an adjustable loop for curetting, and, yet would operate reliably and be manufactured at a modest expense. The tool should posses a means to adjust, the size of the blade with the same hand that is holding the tool, in order to avoid disrupting the procedure. Furthermore, the tool should allow the practitioner to easily lock the size of the curette at a desired size and unlock it to change sizes so that, the cutting tool can be used fixedly without the need for the practitioner to monitor the adjuster.

In view of the sensory-dependent nature of such procedures, the design of the tool used is of critical importance. The curette must have a working element which is sharp enough to cut rather than pull and distort the tissue. Reusable curettes, like those described above, dull over time and do not hold, a sharp edge very well. Thus, a curette which provides a working element of consistent sharpness, which the disposable curette of the present invention provides because of its one-time use, is needed.

It is therefore an object of the present invention to provide a single instrument that can adjust and accommodate various tool head sizes without the need to unnecessarily switch out tools during a procedure.

It is another object of the present invention to provide an instrument that can quickly and easily modulate to accommodate the needs for a particular procedure or procedure.

It is also an object of the present invention, to provide an instrument that can quickly and easily be locked at a desired, cutting head size and unlocked at a desired cutting head size to allow for safe and consistent use of the cutting head.

It is yet another object of the present invention to provide a single curette tool that can be used for a variety of procedures by adjusting the cutting head size to meet the needs of a particular user and/or procedure.

It is a yet further object of the present invention to provide a disposable one-time use curette that can be brought to a procedure and modified for a particular instance or procedure.

BRIEF SUMMARY OF THE INVENTION in view of the foregoing disadvantages inherent in the known curette art, the present invention provides a novel adjustable curette. The general, purpose of the present invention, which will be described subsequently in greater detail is to provide a curette device that is different in that it allows a user to easily adjust a cutting surface size with the movement of a digitally-actuatable (linger/thumb adjustable) adjuster. The adjuster can be easily and conveniently locked or unlocked at a desired cutting surface size. The manual adjustability of a diameter of the hoop blade may lead to improved outcomes in wound debridement. Better control of the cutting surface will allow for more precise debridements and larger surface scraping to be done with a single tool. Further, a flexible steel wire may be easy to manufacture at a low cost.

In a preferred embodiment of the present invention, it is an object to provide an improved dermal curette which may be easily adjusted from 1 mm to 8 mm to be utilized in scraping the biofilm, slough, debris, and devitalized tissue from a chronic wound; as well as lesions and growths from the surface of a patient's skin. It is another object to provide an improved dermal curette having a working edge of consistent sharpness through all available size configurations which is capable of producing a scraping action when used for multiple purposes, such as in removing biofilm, slough, debris, and devitalized tissue from a chronic wound; as well as lesions from the surface of a patient's skin. It is a further object of this invention to provide an improved dermal curette having the ability to save healthcare dollars, improved outcomes through a more thorough debridement based on the easily adjustable hoop cutting surface.

The cutter should be stiff enough in both the axis along the length of the tool as well as laterally so that it may remove tissue without bending or twisting. The handle of the tool should be about the length of a pen so that it may be held like one. For the removal of cancerous or unwanted tissues, the practitioner relies on subtle haptic (touch) sense to differentiate between the stiffness of the unwanted tissue and the healthy tissue. As such, it is important, that there is evenly distributed weight, or at least consistent, weighting throughout the tool, to prevent any moment arm force from the tool itself.

Practitioner may adjust size with the hand performing the procedure (and not have to switch hands).

The curette should have a handle of sufficient weight to provide the balance necessary to allow the physician to properly "feel" the varying resistance levels between biofilm, slough, devitalized tissue and healthy tissue, and an overall design which provides the physician with maximum control of the tool in use. Furthermore, what makes this design of a dermal curette unique is the ability to adjust the size of the cutting surface. Today, disposable curettes are supplied in single size options from 1 mm to 10 mm. Each is stored, in a single use sterile plastic container. If a procedure requires the use of multiple blade sizes, multiple units must be opened requiring discard after use. Having a single disposable and adjustable dermal curette in the hands of a skilled provider will lead to better overall outcomes.

The present invention has been developed in response to that need, and provides an improved dermal curette having a working edge with consistent sharpness which is suitable for scraping procedures, a hooped blade that is adjustable and locks in useful sizes from 1 mm to 8 mm and a handle which is properly balanced and also designed to easily change the size of the cutting surface throughout a procedure to allow the user maximum control of the curette with less waste due to not needing to open multiple unit.

The present invention holds significant improvements and serves as a manually adjustable and disposable curette. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, adjustable curette, constructed and operative according to the teachings of the present invention.

FIG. 4A shows a close-up frontal view of the distal end of the handle of the adjustable curette comprising the triangular profile having a blade opening for allowing both ends of an inwardly bent blade to pass there-through according to an embodiment of the present invention of FIGS. 1 and 3A.

FIG. 4B shows a close-up perspective view of the distal end of the handle of the adjustable curette comprising the "Y" head profile comprising a guide having a first side and a second side according to an embodiment of the present invention of FIGS. 2 and 3B.

FIG. 17 shows a top view of a blade end of the present invention.

FIG. 17A shows a side view of a docking port of the present invention with a cross-sectional view illustrated next thereto.

FIG. 17B shows a top view of an exploded version of a blade docking system of the present invention.

FIG. 17C shows a top view of a blade docking system of the present invention.

DETAILED DESCRIPTION

Figure 1:
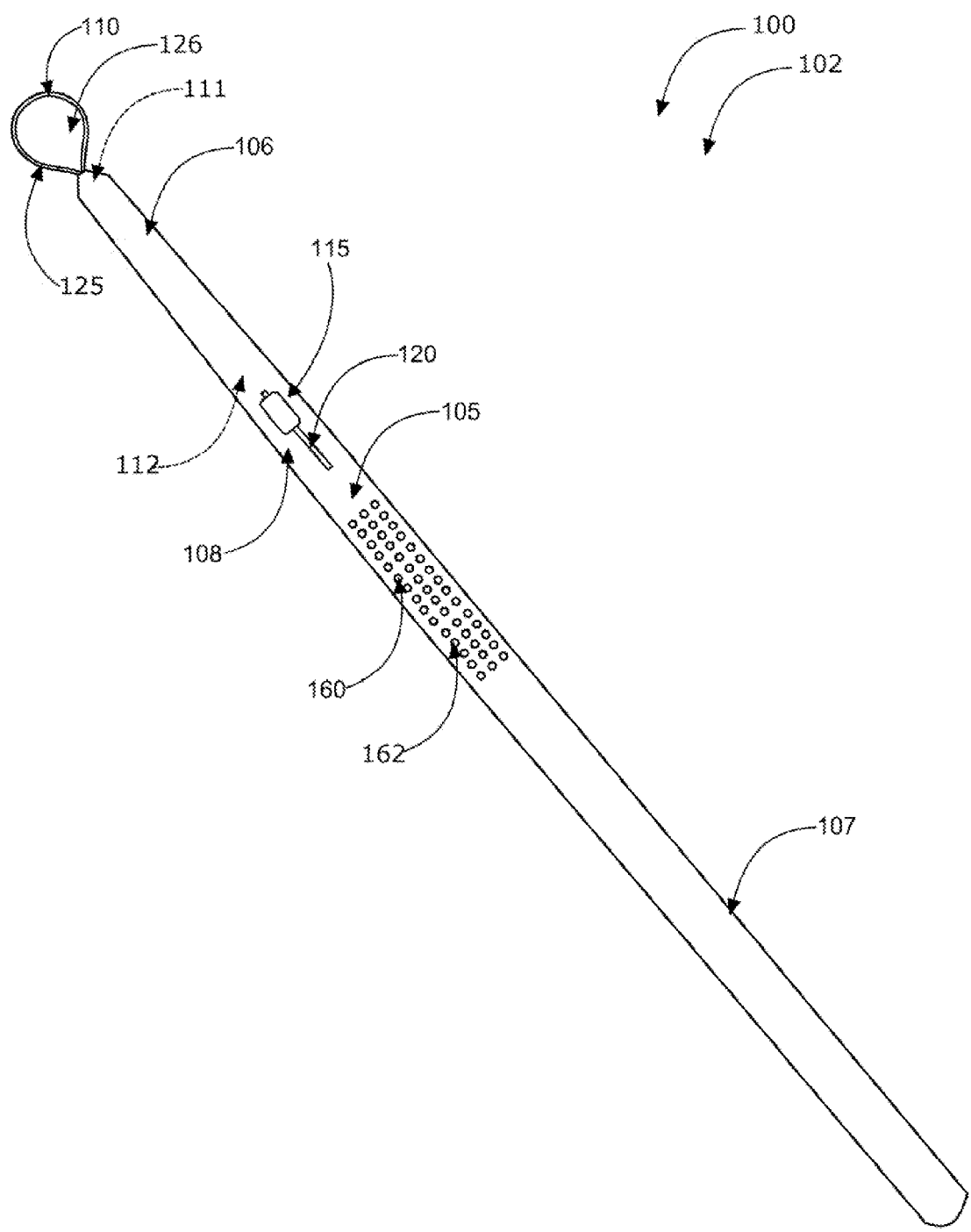
FIG. 1 shows a perspective view illustrating an adjustable curette comprising a handle having a triangular profile according to a preferred embodiment of the present invention.

As discussed above, embodiments of the present invention relate to a adjustable curette and more particularly to a disposable and manually adjustable dermal curette designed to be used in debriding a chronic wound by scraping slough, biofilm, devitalized tissue; as well as lesions and unhealthy tissues from the surface of a patient's skin.

In an embodiment of the present invention, the adjustable curette may comprise a plastic handle having a proximal end portion, a mid-section portion and a distal end portion with a generally circular or looped-shaped working element attached to the distal end portion. For control of the cutting surface size, a slider tab on the handle may be adjustable with the thumb (or other digit) through a series of indents intended to lock the blade into the designated size from 5 μm to 50 cm, preferably, 1 mm through 10 mm, and in preferred embodiments for certain dermal curettes 2 mm to 7 mm. The handle may be provided with a textured surface, preferably grooved or ribbed surface, extending lengthwise along the distal end portion for ease of handling the curette handle. Further, the proximal end of handle portion preferably tapers inwardly to form a flat-nosed surface at its end. The adjustable hoop blade may be attached to the thumb tab as such when the tab is extended toward the distal (hooped cutting edge) end of the handle and the blade size expands to its largest diameter of 10 mm as the thumb slider tab is moved aft, the hoop blade is retracted and the hoop is squeezed against the fixed handle opening and thus contracts to the smallest 1 mm size.

The various set modes of the blade size can be predetermined in unitary loop sizes, i.e. 1 mm, 2 mm, 3 mm, . . . 10 mm, etc. Another means of obtaining predetermined loop sizes is to have predetermined loop sizes that increase the loop diameter in a percentage fashion, i.e. with regularly spaced notches such that each next size is a predetermined percentage larger than the last (i.e. 1 mm, +100% to 2 mm, +50% to 3 mm, etc.). Preferably, there will be markers along the handle and/or along the blade indicating the size of the current blade loop available for procedure. The indicator on the handle, for instance, may be along the slider button channel on the exterior of the handle. If placed on the blade, the portion of the blade next to the distal end of the handle and/or guide will have an indicator etched, or drawn or laser etched or painted onto blade with various sizes, similar to a ruler.

The target uses for the present invention is wound debridement and dermatology. However, further research has covered other uses for the exact same device: MOHS Surgery, Plastic surgery and General Surgery. A similar non-sterile version can be produced to meet several arts and crafts needs: Pumpkin carving, Clay and other medium sculpting, Etching, and Ice Sculpting (with a current run through the blade to produce heat). Curettes being useful in numerous applications require that the present invention include various embodiments for other uses, i.e. smaller loop sizes for ophthalmologic use, and larger loop sizes for shop work. Various sizes and blade type would also be developed for otological curette embodiment (ear), Ophthalmology (eye). Dental plaque removal, and internal uses such as obstetric and gynecology (i.e. dilate and curettage procedure), and possible veterinary surgery.

The cutting blade may also use a variation of the above method to adjust size. The variation may anchor the blade inside the handle and have a sleeve that glides over the surface of the flexible steel to accomplish the task of changing the hoop's size. This method may have the steel blade expand as the sleeve moves aft and contract as the sleeve moves forward. The blade itself may be housed inside the handle, thus only exposing the cutting edge at the appropriately desired size determined by the provider and locked into place by indentations.

While an acceptable blade for the purposes of this invention may include any structurally stiff material that can be pressed, extruded, etc. into a generally planar shape with a sharp-like edge, the preferred embodiment utilizes a blade made of metal, preferably a shape-memory alloy such as nickel titanium, (or nitinol). In this manner the shape, or shapes, of the blade loop can be preconfigured based on loop sizes, in addition, any curvature of the blade can be preconfigured into the blade material. Further enhancements with a shape-memory blade can also allow for the loop to maintain a usable shape and to prevent the loop from curving back or in other ways becoming less useful for its intended operation as a normal curette.

Another preferred embodiment for the blade includes any material that can be made into a wire, preferably for embodiments where the loop size is to be kept small. For instance, for ophthalmological scale, curette blade loop sizes might start at 5 μm or smaller. For clay pottery, sizes might reach as high as 50 cm. Typically, the blade size and grade will be modified based on the loop size. For instance a higher gauge metal would be used for a larger blade size, based on loop size and/or intended use, where as a small gauge or wire would be used for smaller embodiments.

In some embodiments, it may be necessary to choose a blade material, that acts as a mild resistor to allow for heat-generation when a current is passed through. By sending electricity through the blade it could also be used to instantly cauterize a wound or incision. The blade acting as a simple resistance circuit. Possible materials include tungsten, tungsten carbide, titanium, and other metals known in the art for supplying cauterization.

The mid-section portion, of the handle may be defined by a recessed flat surface extending lengthwise along the top of the mid-section portion; the remainder of the mid-section portion is generally cylindrical in shape. For maximum control and proper balance, the proximal end portion may further be provided with a textured surface similar to the distal end portion and the raid-section portion may further be provided with, a finely textured surface extending around its width. Finally, the working element is provided with one cutting edge, which is sharpened to a degree necessary to be used in debriding a chronic wound by scraping slough, biofilm, devitalized, tissue; as well as lesions and unhealthy tissues from the surface of a patient's skin. This cutting edge may be uniformly sharpened to include all potential hoop sizes.

The adjustable curette of the present embodiment of the invention may employ two potential mechanisms for manual blade adjustment. A first mechanism comprises an anchor point that is fixed inside the handle and an adjustable sleeve which may be moved forward to decrease blade diameter size or aft to increase blade diameter size. It is important to note that flexibility of the steel both yields to change size and maintains strength to provide and sharp cutting surface.

A second mechanism comprises the anchor point of the hoop blade being fixed to the adjustable thumb slider. As the thumb slider moves forward, more hoop is exposed, and the fixed opening of the handle provides resistance against the blade. As the thumb slider moves aft, it pulls the blade into the handle, thus decreasing the hoop's diameter against the fixed, handle opening. Both mechanisms rely on the flexibility of a blade folded on itself to produce a hooped, end. The method to adjust the size is unique to either design.

Referring to the drawings by numerals of reference there is shown in FIG. 1 a perspective view illustrating adjustable curette 100 comprising handle 105 having triangular profile 102 according to a preferred embodiment of the present invention. In this embodiment, adjustable curette 100 is shown comprising handle 105 having distal end 106 and proximal end 107 and longitudinal axis 108 running the length of the handle from distal to proximal end. Adjustable curette 100 further comprises blade 110. Blade 110 may comprise a flexible elongated planar member oriented in profile as shown. Blade 110 may comprise fixed end 111 and movable end 112 (not shown, affixed to sliding mechanism within handle body) and may be coupled with handle 105 such that fixed end 111 of blade 110 is fixedly coupled to handle 105 and movable end 112 of blade 110 is coupled to slider 115. It should be noted and appreciated that slider 115 may be movably coupled to handle 105 in alternate embodiments of the present invention. Further, handle 105 may comprise sliding channel 120 situated longitudinally along handle axis 108. Blade 110, when coupled to handle 105 bends inwardly and forms adjustable loop 125 extending beyond distal end 106 of handle 105, as shown.

In continuing to refer to FIG. 1, handle 105 may comprise slider button 115. Slider button 115 is structured and arranged in a variety of manners as disclosed herein for traversing sliding channel 120 such that an adjustment of slider button 115 has a proportionate adjustment to loop area 126 of adjustable loop 125. In such a manner, a user may conveniently change a size of adjustable loop 125 during use of adjustable curette 100. It should be appreciated that, adjustable curette 100 is structured and arranged such that moving slider 115 upwards increases loop area 126 and moving slider 115 downwards decreases loop area 126.

As may further be seen in FIG. 1, handle 105 having triangular profile 102 (shown more fully in FIG. 9B, etc, below) may comprise a triangular shape which, may allow handle 105 to be comfortably held like a pencil allowing for a flat surface upon which to place slider to be actuated by user. Further, the triangular shape may also prevent unintentional rolling of the device while in use, or when placed on a surface. Surface pattern 160 may include a textured ridge on topside of handle 162 of adjustable curette 100 may be necessary as an indicator of a correct orientation. In order to provide ease of use, slider 115 is adjustable using the same hand that handle 105 is held in by user 140, without user 140 having to adjust a hand position too much from a working position. For ergonomic gripping, handle 105 may comprise surface pattern 160 for augmenting dexterity and manipulation of adjustable curette 100. In one embodiment as shown in FIG. 1, surface pattern 160 may comprise plurality of dimples. Dimples may be useful for providing a grip for user 140 when handling adjustable curette 100. Preferably, fixed end 111 of blade 110 may be fixedly mounted to an interior wall of handle 105. The interior wall that fixed end 111 of blade 110 is fixedly mounted may be the wall opposite sliding channel 120. In such a manner, movable end 112 of blade 110 that is mounted to slider 115 which traverses sliding channel 121) may be moved toward distal end 106 of handle 105 for increasing loop area 126 of adjustable loop 125.

Figure 2:
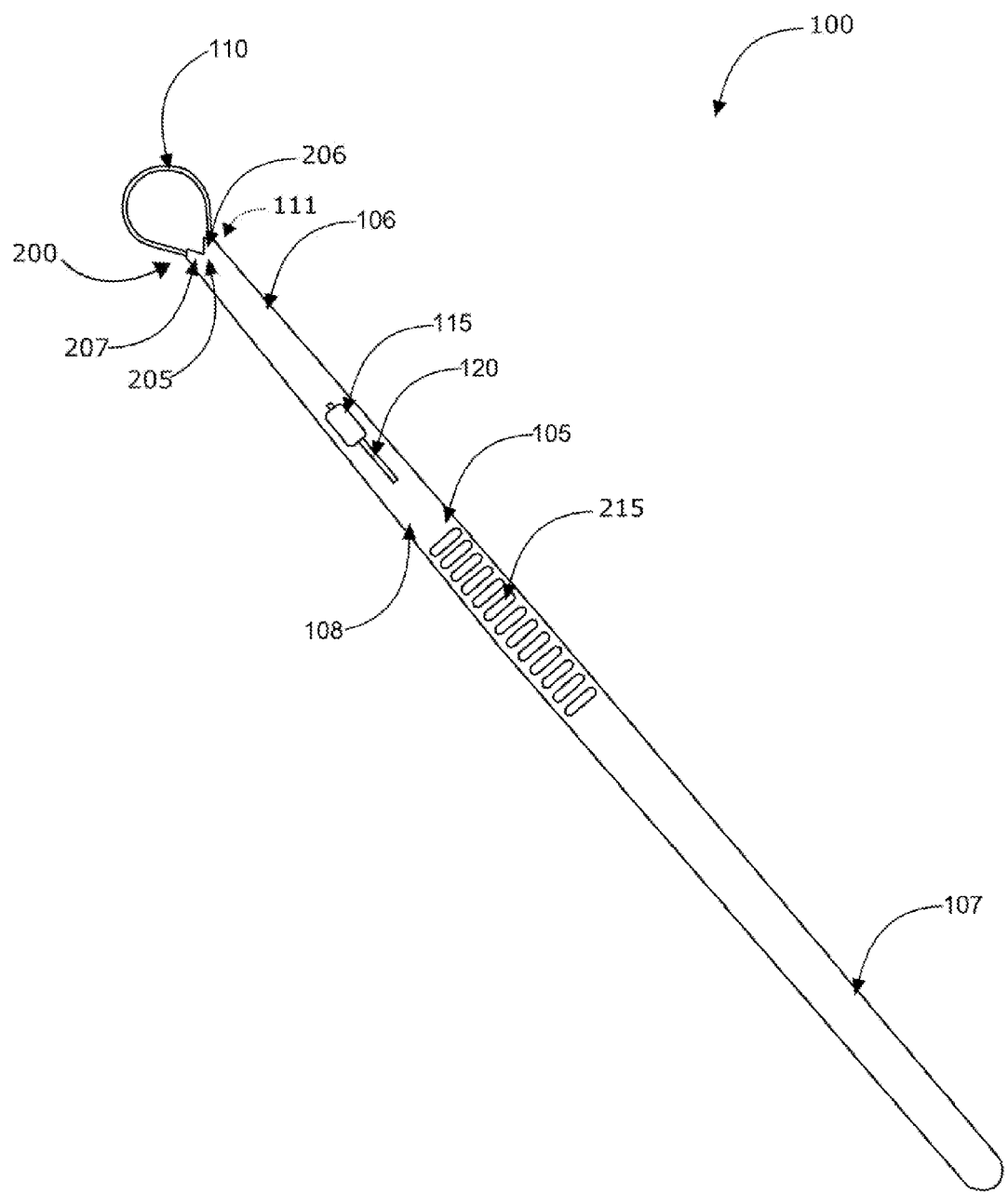
FIG. 2 shows a perspective view illustrating the adjustable curette in an alternative embodiment of the present invention comprising the handle having a "Y" head profile.

Referring now to FIG. 2 showing an alternative embodiment of the present invention comprising handle 105 having "Y" head profile 200. As shown, distal end 106 of handle may comprise guide 205. Guide 205 may be made from two distinct sides: first side 206 to control the angle at which blade 110 adjacent to fixed end 111 orients relative to the longitudinal axis of handle 105; and second side 207, one or both sides oriented to control the angle at which blade 110 adjacent to movable end 132 orients relative to longitudinal axis of handle 105. It should be noted that guide 205 provides for at least a portion of blade 110 to pass through to form adjustable loop. As shown, blade 110 may travel through blade opening of first side 207 and follow affixedly through blade opening of second side 206 thereby forming adjustable loop 125 in front of distal end 106 of handle 105. It should be noted that handle 105 comprising "Y" head profile 200 may be optimal for working with a larger and wider loop areas of adjustable loop because first side 206 and second side 207 of guide 205 are angled away from each other, as compared to handle comprising triangular profile as shown in FIG. 1 whereby the blade egresses from a single blade opening.

In continuing to refer to FIG. 2, handle 185 of adjustable curette 100 may comprise surface pattern 160 which may comprise ribbing 215. Ribbing 215 may be useful for providing a varying grip for user 140 when handling adjustable curette 100. In addition, ribbing 215 may be useful for indicating a correct orientation of handle 105 during use. In an alternative embodiment, ribbing may extend further along handle, and/or circumscribe the handle.

Figure 3A:
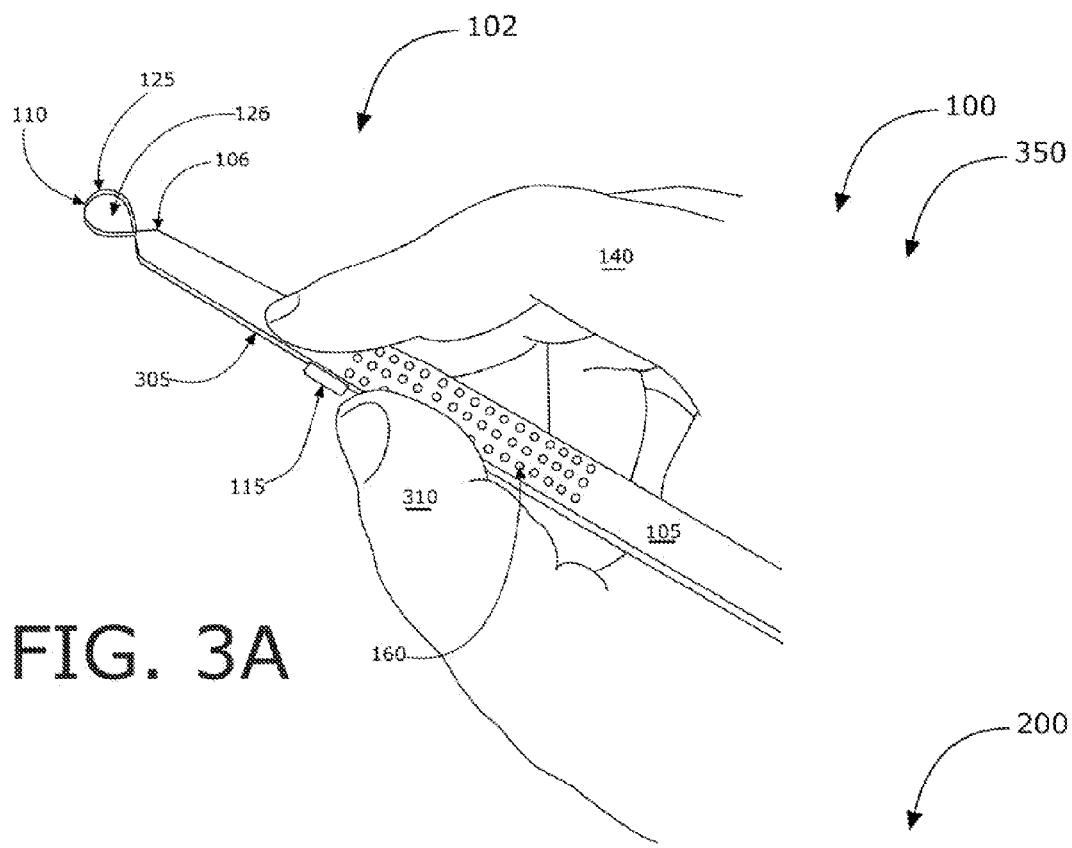
FIG. 3A illustrates a perspective view of the adjustable curette comprising the triangular profile during an 'in-use' condition according to an embodiment of the present invention of FIG. 1.
Figure 3B:
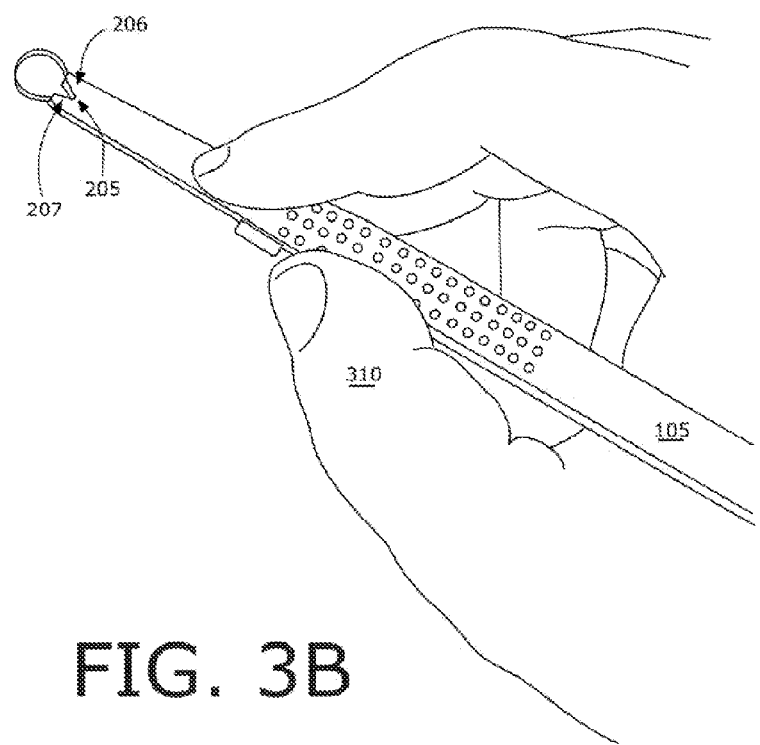
FIG. 3B illustrates a perspective view of the adjustable curette comprising the "Y" head profile during an 'in-use' condition according to an embodiment of the present invention of FIG. 2.

Referring now to FIGS. 3A and 3B showing a perspective view of adjustable curette 100 during 'in-use' condition with user 350 according to an embodiment of the present invention. As shown in FIG. 3A, handle 105 having triangular profile 102 may comprise slider 115 located on thumb side 305 of handle 105 such that it may be actuated by thumb digit 310 of user hand 140 (such as a thumb of user hand 140, as seen in FIG. 3A). Turning to FIG. 3B showing a perspective view of adjustable curette 100 comprising "Y" head profile 200 during 'in-use' condition with user 350 according to an embodiment of the present invention of FIG. 2. Slider 115 may be on thumb side 305 of handle 185 such, that it may be actuated by thumb digit 310 of user 140 (ie. the thumb of user hand 140, as shown).

In continuing to refer to FIG. 3A, it may be appreciated that handle 105 comprising triangle profile 182 may be held and manipulated by user 140 similar to a pen or pencil during 'in-use' condition by user 350.

Referring now to FIG. 4A showing a close-up perspective view of adjustable curette 100 comprising triangular profile 102 having blade opening 410 for allowing both ends of the inwardly bent blade to pass there-through according to an embodiment of the present invention. As shown, distal end 106 of handle 105 has a triangular profile 102, where the distal end surface allows for blade opening 410. Blade opening 410 may be a slit/opening for allowing a blade bent inwardly, to pass through blade opening 410 twice.

In referring now to FIG. 4B showing a close-up perspective view of adjustable curette 100 comprising "Y" head profile 200 comprising guide 205 having first guide side 206 and second guide side 207 according to an embodiment of the present invention. As shown, distal end 106 of handle 105 includes a "Y" head profile 200 having separated ends and openings for each end of the blade. First side 206 having blade opening 410 and second side 207 having blade opening 410. Blade opening 410 may comprise a slit/opening for allowing blade 110 to pass there-through. In the embodiment of the present invention of FIG. 4B, the fixed end of a blade may be fixedly mounted to second side 207 of guide 205 and movable end 112 of blade 110 may be securely attached to slider 115. It should be noted that blade 110 passing through blade opening 410 of second side 207 of guide 205 is stationary and blade 110 passing through blade opening 410 of first side 206 of guide 205 ingresses and egresses as slider 115 is adjusted by user 140. In an alternative embodiment; both ends of the blade may be fixed and enter through respective guide sides.

Figure 5A:
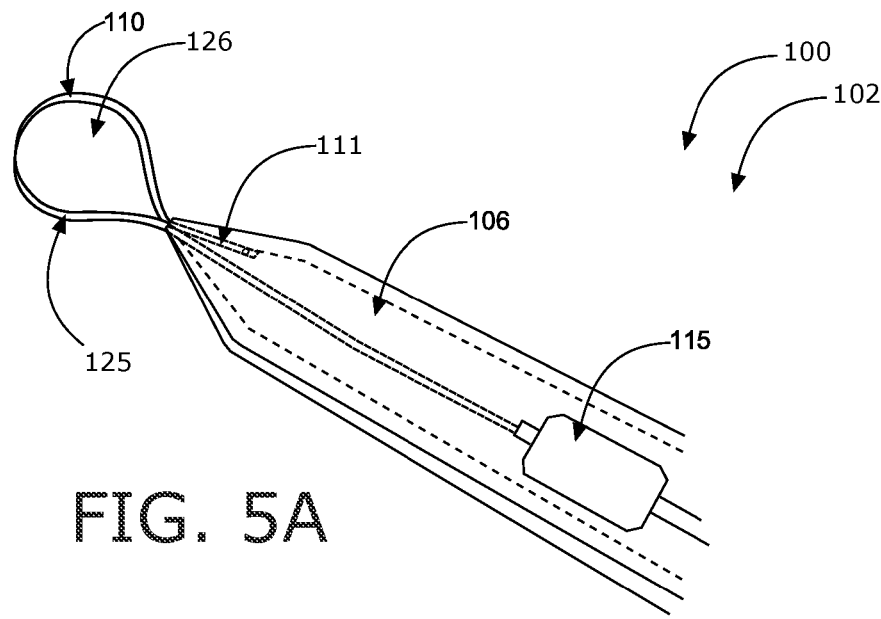
FIG. 5A is an interior perspective view of the handle of the adjustable curette comprising the blade controlled by an adjustable slider according to an embodiments of the present invention of FIGS. 1, 3A, and 4A.

In referring now to FIG. 5A illustrating an interior perspective view of handle 105 of adjustable curette 100 having triangular profile 102 and comprising blade 110 which is user-manipulable via slider 115 according to an embodiment of the present invention. Distal end 106 tapers to a slit or single blade opening 410. In one embodiment, movable end 112 of blade 110 may be fixedly mounted to slider 115 such that blade 110, folded onto itself inside handle 105, is able to slide in and out of blade opening 410 of distal end 106 of handle 105 for forming adjustable loop 125. It should be appreciated that loop area 126 of adjustable loop 125 is increasable and decreasable via an adjustment of slider button 115 as slider 115 is moved through sliding channel 120. It may further be seen that sliding channel 120 may traverse longitudinal axis 108 of handle 105.

Figure 5B:
FIG. 5B is a perspective view of the blade as shown in FIG. 5A demonstrating blade holes according to an embodiment of the present invention of FIG. 5A.
Figure 5C:
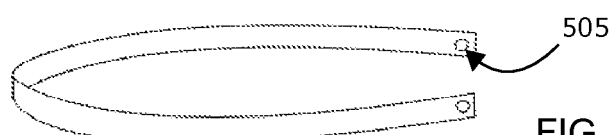
FIG. 5C is a perspective view of the blade demonstrating blade bent inwardly according to another embodiment of the present invention.
Figure 5D:
FIG. 5D is a perspective view of the blade demonstrating blade bent according to another embodiment of the present invention.
Figure 5E:
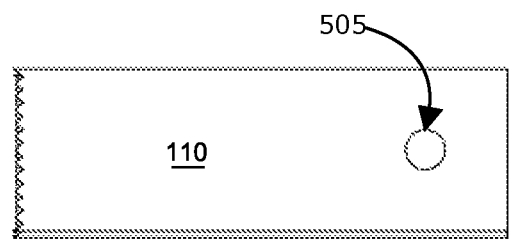
FIG. 5E is a close-up perspective view illustrating a first blade end and a second blade end shown in FIG. 5D according to an embodiment of the present invention.
Figure 5F:
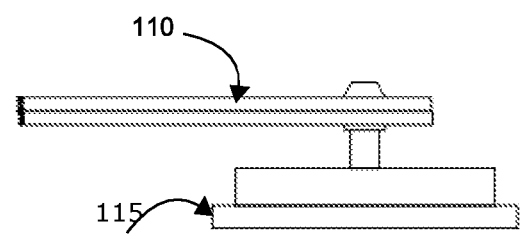
FIG. 5F shows a top perspective view illustrating the blade of FIG. 5E attached to the slider according to an embodiment of the present invention.

In referring now to FIGS. 5B and 5C showing views of blade 110 comprising blade hole(s) 505 located at each end of blade 110 according to an embodiment of the present invention. As shown, blade 110 may be bent inwardly for forming adjustable loop 125. Preferably, blade 110 is bent inwardly such that blade hole(s) 505 are in direct alignment, as shown in FIG. 5C. FIG. 5B shows the same blade in three arrangements, from straight bent to mated bent. When blade is mated, holes 505 may align for a single boss or pin to capture and secure both ends of blade within the handle. When the blade securing mechanism, or securer, is affixed, a separate sliding sleeve, as seen in a later embodiment of the present invention, below as in FIGS. 14A and 14B. In an alternative embodiment, the securer may be attached directly to a slider, as seen in FIG. 5D, FIG. 5D shows a top perspective view illustrating blade 110 attached to slider 115 according to an embodiment of the present invention. As shown, blade 110 may be fixedly attached to slider 115 via blade securer 510. In one embodiment, blade securer 510 may comprise a pin having a bolt and a washer. The pin may be connected to slider 115 and may be insertable through blade hole(s) 505 of blade 110. The pin may be secured to blade 110 via the bolt and the washer. In other embodiments, blade securer 510 may also comprise a clip, a fastener, a staple, or a high-bond adhesive.

As can be seen, in the embodiment of the invention including a blade, particularly as shown in FIG. 5B, the preferred blade for the present invention is a planar body with two elongated edges. The blade is preferable dual-sided, in that it is meant to cut in a first or second direction (when the tool is rotated or flipped). Both edges of the blade preferably serve as a curette, in embodiments deploying a wire as blade, this multi-directional cutting is present and even more pronounced. Depending on the orientation and shape of the handle, it may be useful to switch to the other blade edge to get a better feel or reach to cut. Also, if during the procedure the blade dulls, becomes occluded or encrusted by debris, the tool should allow the user to flip/rotate the handle to use the alternate blade edge.

Figures 6A, 6B:
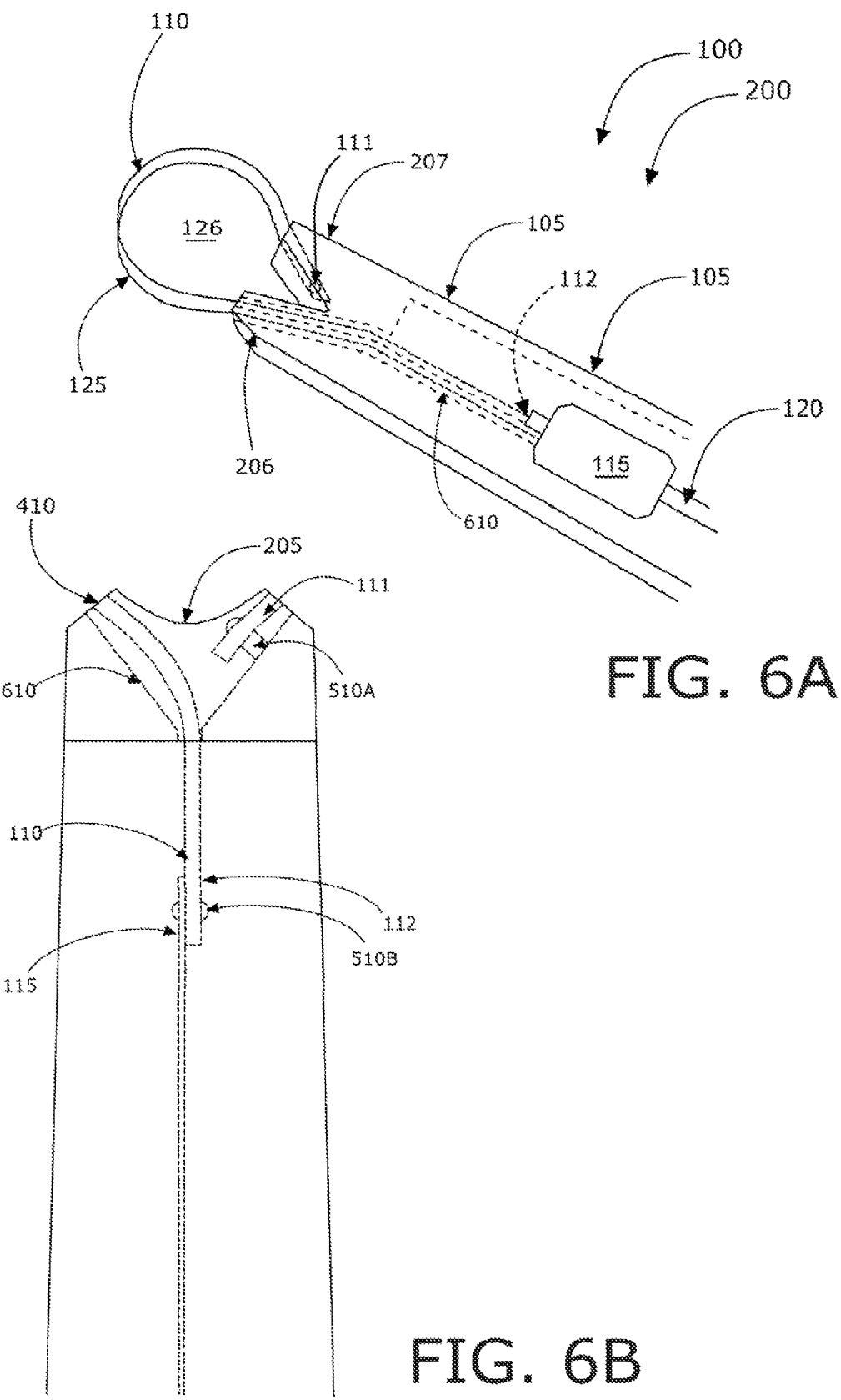
FIG. 6A shows an interior perspective view of the handle of the adjustable curette comprising the "Y" head profile and comprising the blade controlled by the adjustable slider according to an embodiment of the present invention of FIGS. 2, 3B, and 4B.
FIG. 6B shows a close-up top-view of an interior portion of the adjustable curette handle distal end comprising the "Y" head profile from a top angle showing a fixed end of the blade fixedly mounted to a second side of the guide according to an embodiment of the present invention of FIG. 6A.

In referring now to FIGS. 6A-6B showing an interior perspective view of handle 105 of adjustable curette 100 comprising "Y" head profile 200 and having blade 110 controlled by slider 115 according to an embodiment of the present invention shows another interior view of adjustable curette 100 comprising "Y" head profile 200 from a top angle. As shown, fixed end 111 of blade 110 may be fixedly mounted to second side 207 of guide 205 and movable end 112 of blade 110 may be securely attached to slider 115. It should be noted that blade 110 passing through blade opening 410 of second side 207 of guide 205 is stationary and blade 118 passing through blade opening 410 of first side 206 of guide 205 is able to slide in and out of blade opening 410 as slider 115 is adjusted up and down by user 148 thus arranging blade loop 125 and size of area 126. Slider 115 moves along channel 120 and in cavity 610.

As seen in FIG. 6B, blade 110 may be fixed to slider 115 at post 510 at movable end 112. Blade 110 follows into cavity 610 in handle and out opening 410 at distal end 205. Blade fixed end 111 re-enters cavity 610, preferably through, separate opening from 410 (but may be a single opening over entire surface of distal end) and affixes to post 510A.

Figure 7A:
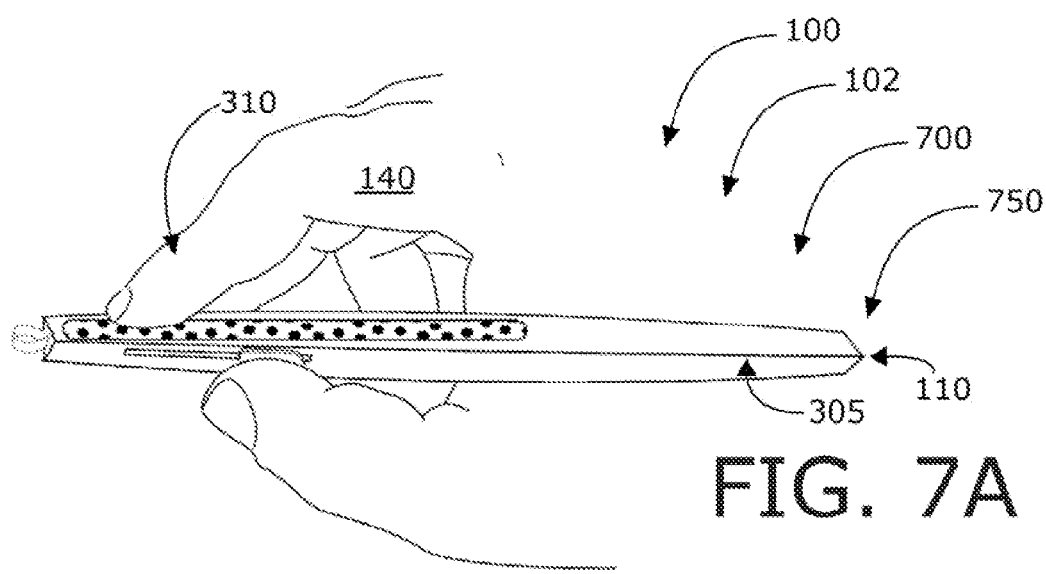
FIG. 7A shows a side view of the adjustable curette comprising the triangular profile during an 'in-use' condition showing the adjustable slider on a thumb side of the handle for adjustment by a thumb of the user and comprising the adjustable loop having a small loop area according to an embodiment of the present invention.
Figure 7B:
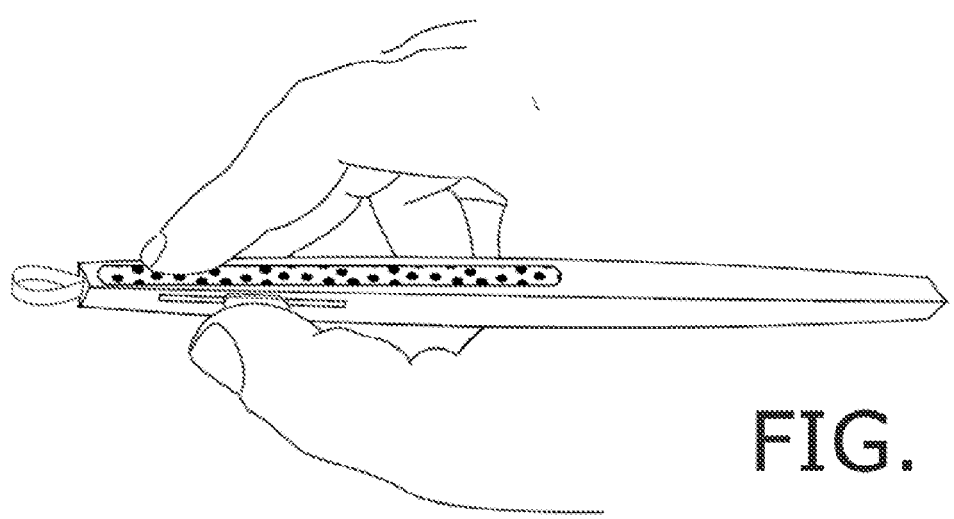
FIG. 7B shows a side view of the adjustable curette of the embodiment shown in FIG. 7A comprising the triangular profile during the 'in-use' condition showing the adjustable slider on the thumb side of the handle for adjustment by the thumb of the user and comprising the adjustable loop having a medium loop area according to an embodiment of the present invention.
Figure 7C:
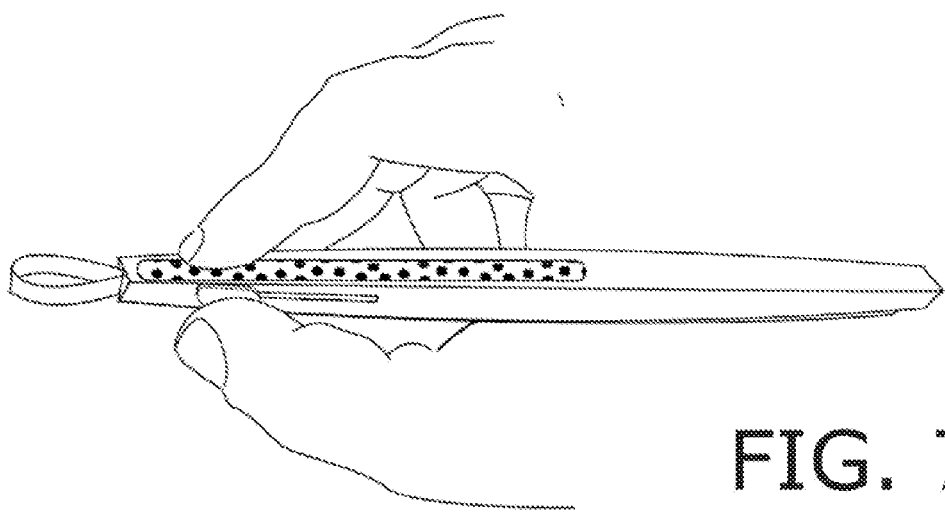
FIG. 7C shows a side view of the adjustable curette of the embodiment shown in FIGS. 7A and 7B comprising the triangular profile during the 'in-use' condition showing the adjustable slider on the thumb side of the handle for adjustment by the thumb of the user and comprising the adjustable loop having a large loop area according to an embodiment of the present invention.

In referring now to FIGS. 7A-C showing several perspective views of thumb slide adjuster embodiment 700 of adjustable curette 100 comprising triangular profile 102 during 'in-use' condition 750 according to an embodiment of the present invention. As shown, handle 185 may comprise slider 115 located on thumb side 305 of handle 105 for adjustment by the thumb of user 140. As seen in FIG. 7A, adjustable loop 125 may comprise loop area 126 having a smaller diameter when slider 115 is positioned closer to proximal end 187 of handle 105 of slider channel 120. FIG. 7B shows a perspective view of adjustable curette 100 comprising triangular profile 102 during 'in-use' condition 750 showing slider 115 located on thumb side 305 of handle 105 for adjustment by the thumb 310 of user 140. As shown, adjustable loop 125 may comprise loop area 126 having a medium diameter when slider 115 is positioned in a middle of slider channel 120. FIG. 7C shows a perspective view of adjustable curette 100 comprising triangular profile 102 during 'in-use' condition 750 showing slider 115 located on thumb side 305 of handle 105 for adjustment by the thumb 310 of user 140. As shown, adjustable loop 125 may comprise loop area 126 having a large diameter when slider 115 is positioned closer to distal end 106 of handle 105 of slider channel 120. Top side 710 includes pattern 160 for use of grip and to allow the index finger to further guide procedures.

In continuing to refer to FIGS. 7A-C, handle 105 may comprise surface pattern 160 comprising rubber strip 725. Rubber strip 725 may be located on index finger side 710 of handle 105 according to an embodiment of the present invention. Surface pattern 160 may use dimples or ribbing. It should be appreciated that surface pattern 160 on index linger side 710 of handle 105 may provide an ergonomic gripping surface for an index linger of user 140 during 'in-use' condition 750.

Figure 8A:
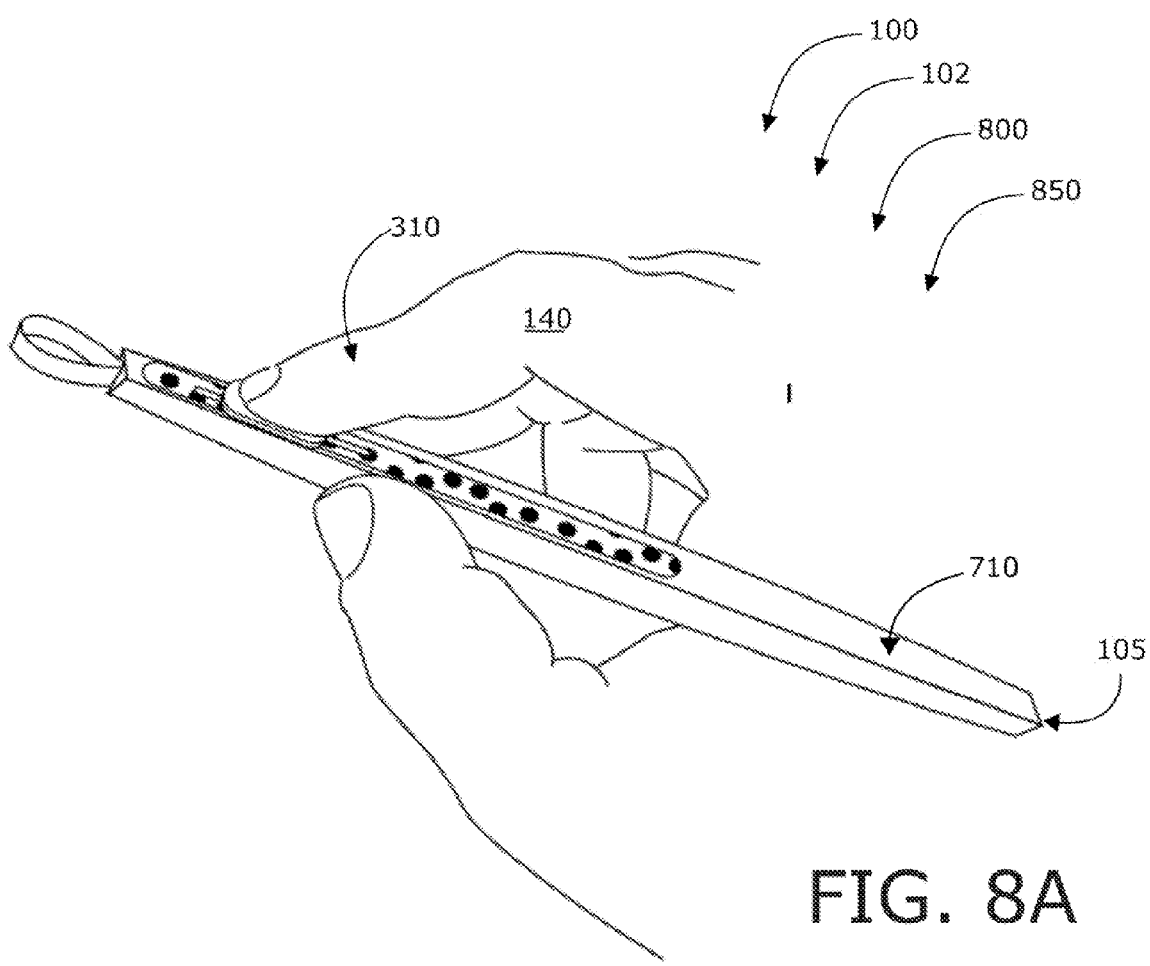
FIG. 8A shows a side view of the adjustable curette comprising the comprising the triangular profile during an 'in-use' condition showing the adjustable slider on a top side of the handle for adjustment by an index finger or other digit of the user according to an embodiment, of the present invention.
Figure 8B:
FIG. 8B shows a side view of the adjustable curette comprising the comprising the triangular profile of FIG. 8A showing the adjustable slider on the top side of the handle for adjustment by the index finger or other digit of the user according to an embodiment of the present invention.

In referring now to FIGS. 8A-B showing a pair of perspective views of index finger slider adjuster embodiment 800 of adjustable curette 100 comprising "Y" head profile 200 during 'in-use' condition 850 illustrating slider 115 on index finger side 710 of handle 105 for adjustment by an index finger or other digit 310 of user hand 140 according to an embodiment of the present invention. FIG. 8B shows another perspective view of adjustable curette 100 comprising "Y" head profile 200 illustrating index linger slider adjuster embodiment 800. It should be appreciated that in this embodiment, user 140 may adjust slider 115 via the index, finger and not the thumb. Index finger slider adjuster embodiment 800 may be ideal for user 140 who is right-handed and alternatively left-handed as index linger side 710 is on a top of handle 105.

Figure 9A:
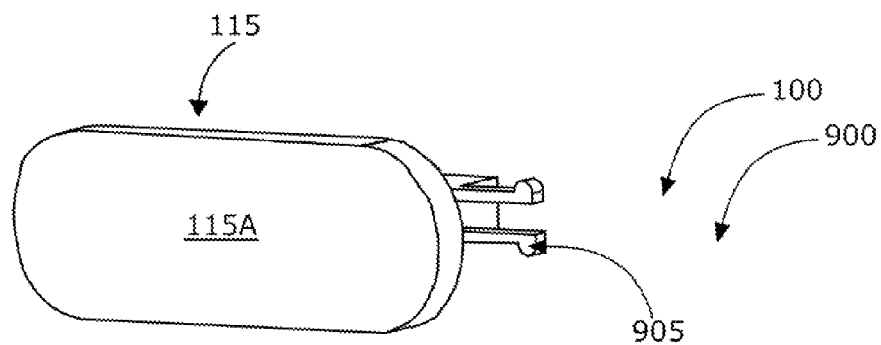
FIG. 9A shows an isolated top perspective view of the adjustable slider button with a zipper size adjuster for a slider rail according to an embodiment of the present invention.
Figure 9B:
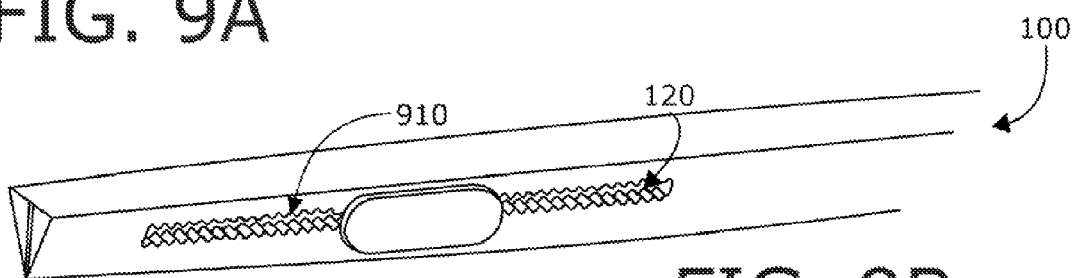
FIG. 9B shows a side view of the adjustable slider of FIG. 9A installed within the sliding rail channel comprising a plurality of grooves according to an embodiment of the present invention.
Figure 9C:
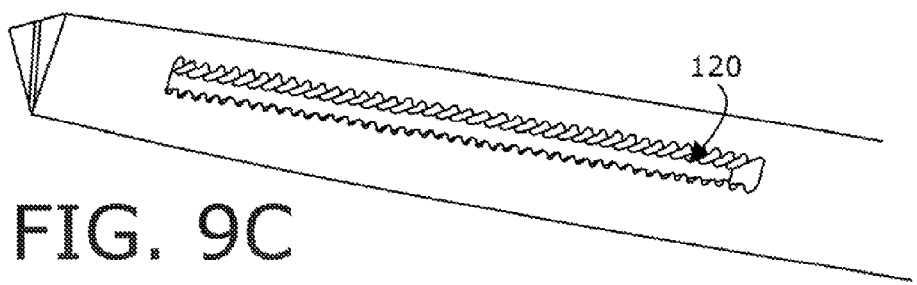
FIG. 9C shows a side view of the sliding rail channel without slider comprising the plurality of grooves according to an embodiment of the present invention.
Figure 9D:
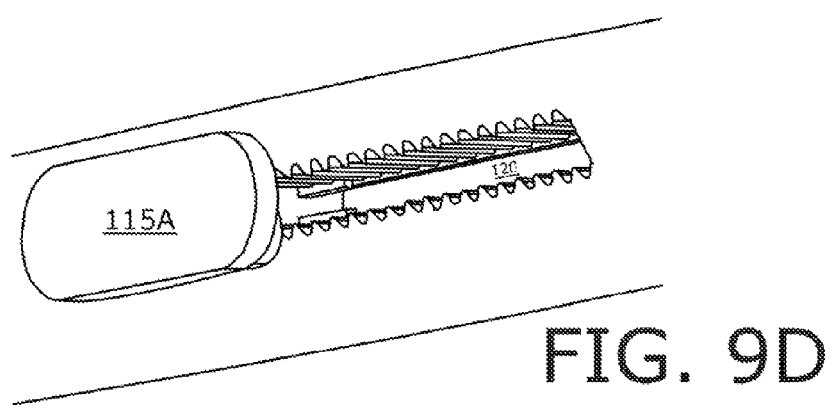
FIG. 9D shows a close-up view of the slider in rail according to an embodiment of the present invention.

In referring now to FIGS. 9A-D showing several perspective views of slider 115 comprising zipper size adjuster 900 according to an embodiment of adjustable curette 100. FIG. 9A is an isolated view illustrating slider 115 with articulable surface 115A of adjustable curette 100 comprising zipper size adjuster 900. As shown, zipper size adjuster 900 may comprise slider rail 905 for interacting with sliding channel 120 of handle 105 comprising plurality of grooves 910. Slider rail 905 may be structured and arranged to removably engage with plurality of grooves 910 as slider 115 is manipulated by user 140 across sliding channel 120. FIG. 9B shows a perspective view of slider 115 comprising zipper size adjuster 900 installed within sliding channel 120 comprising plurality of grooves 910 according to an embodiment of the present invention. FIG. 9C shows an alternative perspective view of sliding channel 120 comprising plurality of grooves 910. FIG. 9D shows an alternative perspective view of zipper size adjuster 900 installed within sliding channel 120 comprising plurality of grooves 910 according to an embodiment of the present invention. It should be noted that zipper size adjuster 900 behaves similarly to a zipper such that user is able to manipulate slider 115 across plurality of grooves 910 comprising opposing teeth of sliding channel 120. User is able to adjust loop area of flexible loop. In addition, when slider 115 is positioned in groove 910, blade and loop area becomes fixed in position.

It should be appreciated in looking and comparing FIGS. 8A-C and FIGS. 9A-B that slider 115 may be on one of the sides of handle 105 comprising thumb side 305 for manipulating slider 115 via a thumb of user 140 and alternatively located on the topside of handle 105 comprising index finger side 710 for manipulating slider 115 via an index finger of user 140. Preferably, slider 115 should be near distal end 106 of handle 105 so that actuating digit 310 may adjust its full length without other fingers holding handle 105 needing to move.

An advantage of placing slider 115 on top of handle 105 is that it is the most ambidextrous solution. If slider 115 is placed on topside of handle, the locking mechanism provided by grooves 910 and complimentary notch of slider rail 905 of slider 115 is important, since digit 310 of user 140 tends to have the most pressure on adjustable curette 100 during scraping, and may unintentionally bump slider 115 during use. The locking mechanism may prevent slider 115 from moving in the event that pressure is placed on slider 115. Further, slider 115 may also be on the side of handle 105, again near distal end 106 of handle 105. As may be seen, slider 115 may be parallel to a face of adjustable curette 100 that it is on. It may also be comfortable if slider 115 on the side is perpendicular to the top lace of adjustable curette 100. In one preferred embodiment, the smallest size of predetermined distance may be 1 mm and have a range of motion not longer than 30 mm (which is more than needed for a range of 1 mm-10 mm loop size) so that digit 310 of user 140 may adjust its full length without, other fingers holding handle 105 having to move. Slider may adjust in 1 mm increments, but may adjust in larger increments regularly, or as the loop size grows it may raise increments in a fester method, i.e. 1, 2, 3, 4, 5, 7, 10, 13, 17, 21, 30, 40 mm, etc.

Figure 10A:
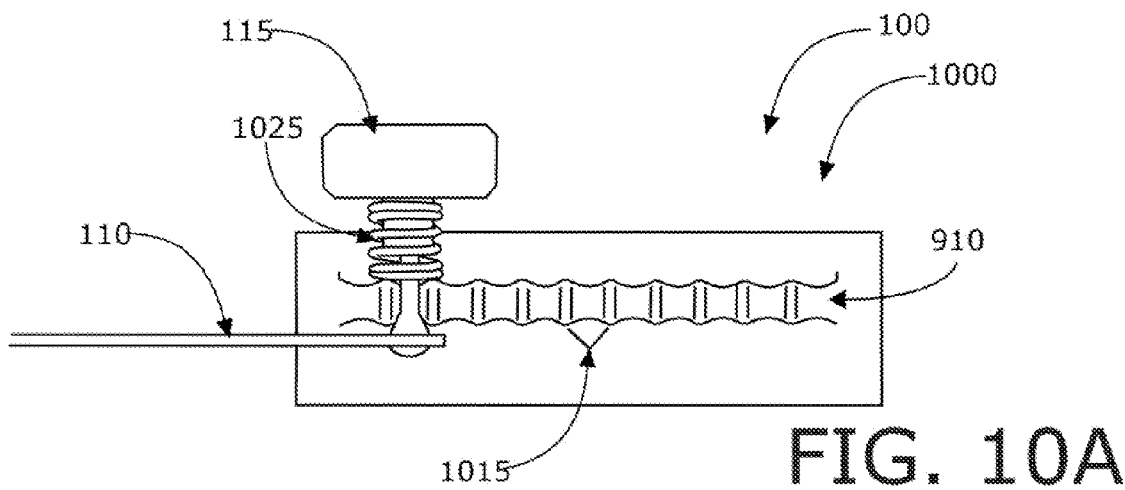
FIG. 10A shows a close-tip cut-out side view of a spring locking mechanism of the present invention comprising a spring and a plurality of grooves spaced apart via a predetermined distance according to an embodiment of the present invention.
Figure 10B:
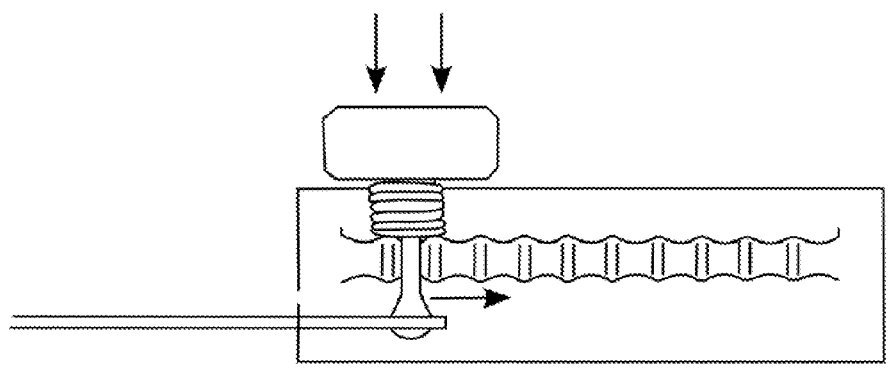
FIG. 10B shows the spring locking mechanism as shown in the embodiment of FIG. 10A for locking the adjustable slider in one of the grooves via a pressing motion of the user according to an embodiment of the present invention in an unlocked position.
Figure 10C:
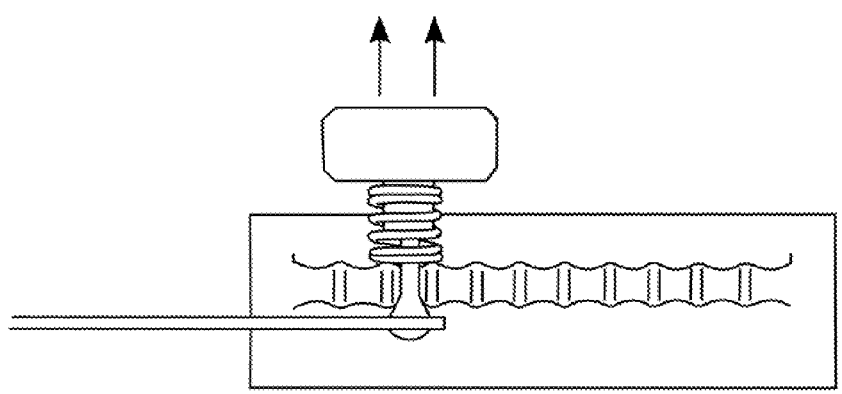
FIG. 10C shows the spring locking mechanism of FIGS. 10A and 10B for unlocking the adjustable slider from one of the grooves via a depressing motion of the user according to an embodiment of the present invention locked in groove.

In referring now to FIGS. 10A-C showing several perspective views of spring locking mechanism 1000 of adjustable curette 100 for locking and unlocking slider 115 in place according to an embodiment of the present invention. As shown in FIG. 10A, spring locking mechanism 1000 may comprise spring 1025 and plurality of grooves 910 spaced apart via predetermined distance 1015. FIG. 10B shows spring locking mechanism 1000 for unlocking slider 115 out of one of plurality of grooves 910 via a pressing motion of user 140 according to an embodiment of the present invention. FIG. 10C shows spring locking mechanism 1000 for locking slider 115 in one of plurality of grooves 910 via a depressing motion of user 140 according to an embodiment of the present invention. Alternatively, the pressing action may lock the slider and blade in place to accommodate an index finger pressure for use of device.

During use, spring locking mechanism 1000 may be advantageous to user 140 for temporarily fixing a user-preferred size of adjustable loop 125 of blade 110. User 140 is able to simply and swiftly adjust loop area 126 of adjustable loop 125 by sliding slider 115 and fix the user-preferred size of adjustable loop 125 by pressing slider 110 inwardly to lock slider 115 in groove 910. Then, user 140 may depress or pull slider to release slider 115 from groove 910 for further adjustment. Having adjustable loop 125 that is fixed may be useful for allowing user 140 to use adjustable curette 100 having the user-preferred size of adjustable loop 125 for a period of time. Further, it may be appreciated that user 140 is able to adjust, lock, and unlock slider 115 using only the working hand of user 149. This may result in saving tremendous time and performing smoother procedures using adjustable curette 100 as user 140 is able to continuously work without pause to sustain work flow and momentum.

In one embodiment of the present invention, predetermined distance 1015 may comprise 1 mm. However, in other embodiments of adjustable curette 100, predetermined distance 1015 may comprise increments as small as 0.1 mm i.e. 1 μm for certain applications.

In one embodiment of the present invention, grooves 910 may comprise complementary labeled indents on an outside of handle 105 to indicate a diameter size of loop area 126 of adjustable loop 125 when slider 115 is in one of plurality of grooves 910. There are several advantages for having labeled indents that indicate the diameter size of adjustable loop 125. For example, user 140 may not have to approximate the size by eye and may know exactly what size is required. With labels, slider 115 may be easily configured to appropriate size of adjustable loop 125. Also, in the event that there are two practitioners for a procedure, one may communicate to the other, "Set curette to 3 mm". The other may easily make the adjustment accordingly by adjusting slider 115 with digit 310 to groove 910 corresponding to 3 mm. Furthermore, user 140 may be required to provide detailed, charting of the procedure including tools used. Practitioners often provide notes that state "used 7 mm and 2 mm curette". This experience may be easily performed having labels indicating various sizes. Lastly, it may improve measurement of a wound size. Related to charting, a practitioner will usually try to approximate the size of a wound, and an accurate adjustable loop 125 may be a visual aid in this measurement.

Figure 11A:
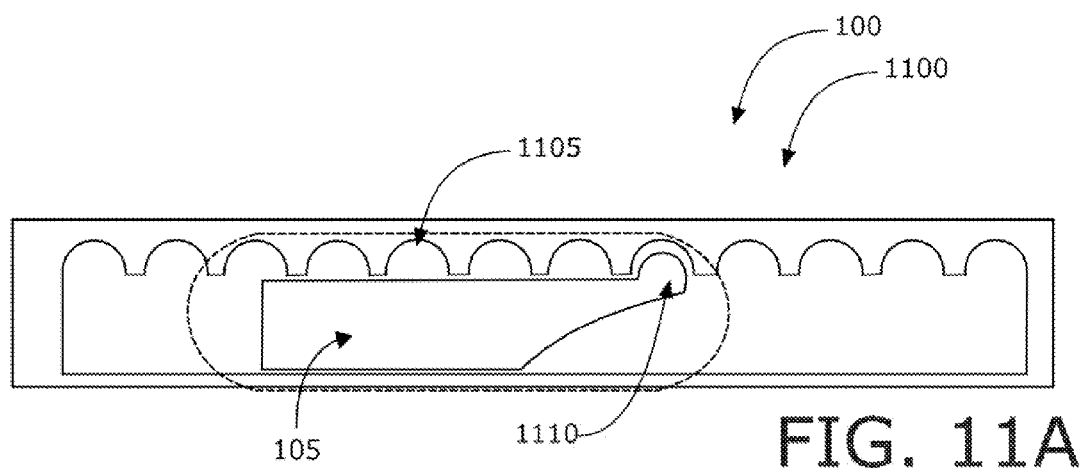
FIG. 11A shows a cut-out side view of a notch locking mechanism of the present invention for actuating the adjustable slider of the adjustable curette according to an embodiment of the present invention.
Figure 11B:
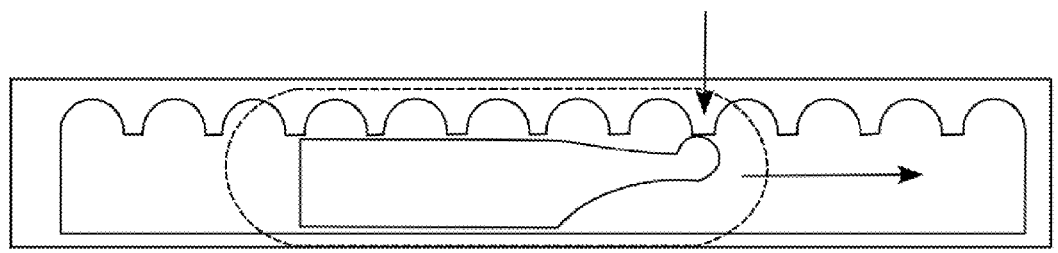
FIG. 11B shows a cut-out side view of the notch locking mechanism comprising a ball connected to the slider and removably-securable into at least one notch according to an embodiment of the present invention.
Figure 11C:
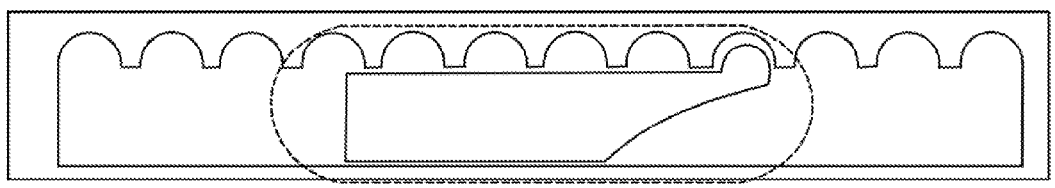
FIG. 11C shows a cut-out side view of the bah secured within one of the notches of the notch locking mechanism according to an embodiment of the present invention.

In referring now to FIGS. 11A-11C showing a notch locking mechanism 1100 for locking and unlocking slider 115 of adjustable curette 100 according to an embodiment of the present invention. FIG. 11B shows a perspective view of notch locking mechanism 1100 comprising ball 1110 connected to slider 115 that is removably-securable into at least one notch 1105. FIG. 11C shows perspective view of ball 1110 secured within 1105 of notch locking mechanism 1100. As shown in FIGS. 11A-11C, notch(es) 1105 may be located across an interior-top of sliding channel 120. Slider 115 comprising ball 1110 may be structured to securely fit inside notch 1105 for temporarily locking slider 115 in place, thus fixing loop area 126 of adjustable loop 125. As shown in FIG. 11B, user 140 may unlock ball 1110 from notch 1105 via a forceful pushing motion on slider 115 until ball 1110 fits into next notch 1105 along slider channel 120. Having adjustable loop 125 that is fixed may be useful for allowing user 140 to use adjustable curette 100 having the user-preferred size of adjustable loop 125 for a period of time. It should be further noted that notch(es) 1105 may be designed to be arranged predetermined distance 1015 from one another as disclosed in FIGS. 10A-C.

Figure 12A:
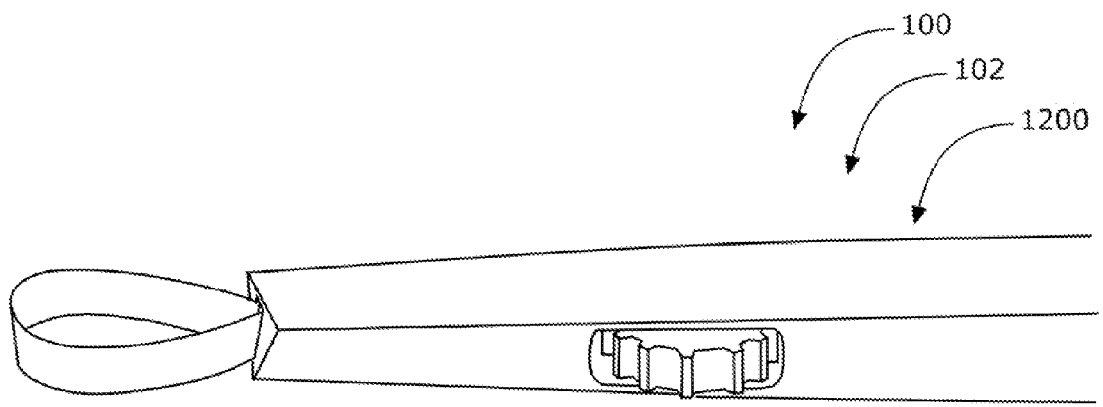
FIG. 12A shows a side view of a stationary wheel slider of the present invention for actuating the adjustable blade of the adjustable curette according to an embodiment of the present invention.
Figure 12B:
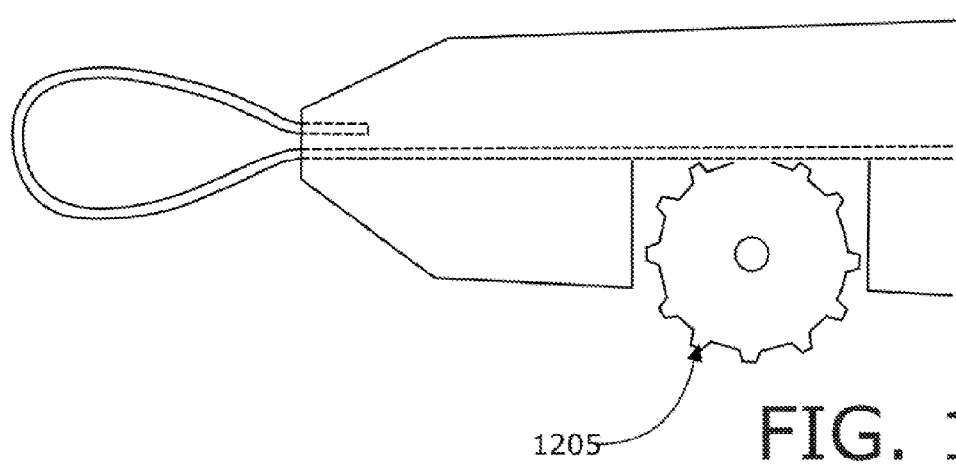
FIG. 12B shows a cut-out top view of a wheel that is rotatable by the user of the wheel size adjuster and comprising a plurality of spokes according to an embodiment of the present invention of FIG. 12A.
Figure 12C:
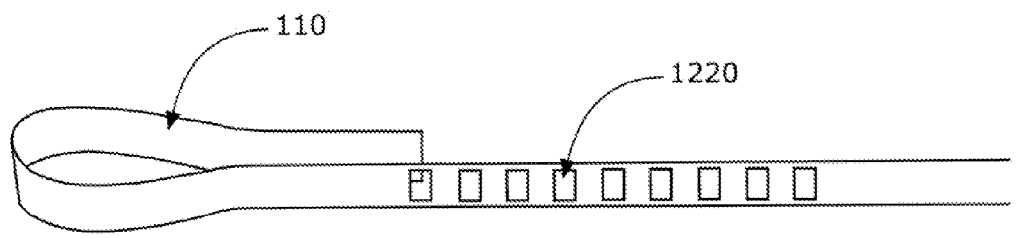
FIG. 12C shows a perspective view of the blade comprising a plurality of sprocket holes for receiving the spokes of the wheel of the wheel size adjuster according to an embodiment of the present invention of FIGS. 12A and 12B.

Referring now to FIGS. 12A-C showing wheel size adjuster 1200 for actuating slider 115 of adjustable curette 100 according to art embodiment of the present invention. As shown in FIG. 12A, thumb side 305 of handle 105 may comprise wheel 1205 for controlling blade 110 and adjusting a size and shape of loop area 126 of adjustable loop 125.

FIG. 12B shows wheel 1205 that is rotatable by user 140 for controlling blade 110 according to an embodiment of the present invention of FIG. 12A. As shown, wheel 1285 may comprise plurality of spokes 1205. Spokes 1205 may be useful, for contacting and moving blade 110 comprising complementary sprocket holes 1220 as illustrated in FIG. 12C. Plurality of sprocket holes 1220 may be structured and arranged for receiving spokes 1205 of wheel 1205 of wheel size adjuster 1200 for actuating slider 115 of adjustable curette 180 according to an embodiment of the present invention. It should be noted that sprocket holes 1220 may be arranged predetermined distance from one another, it should be noted that the term slider in this description is meant as a general term to comprise all sons of methods to move one end of the blade and/or manipulate the size of the blade loop.

Figure 13A:
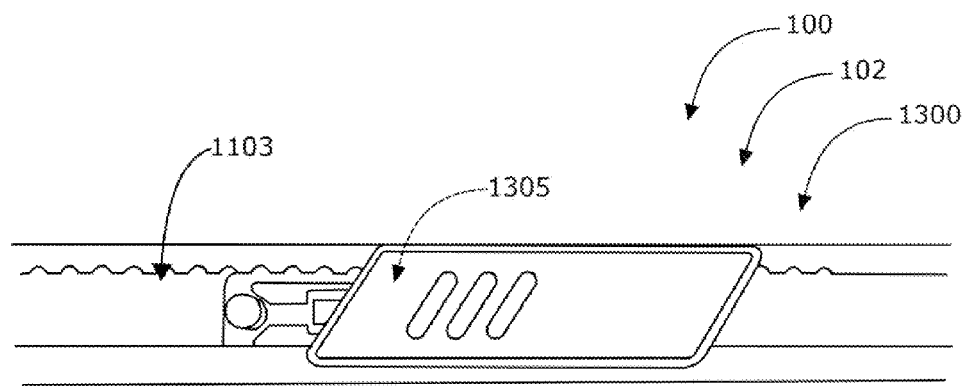
FIG. 13A shows a close-up top view of a leaf spring size adjuster for actuating the adjustable slider of the adjustable curette according to an embodiment of the present invention.
Figure 13B:
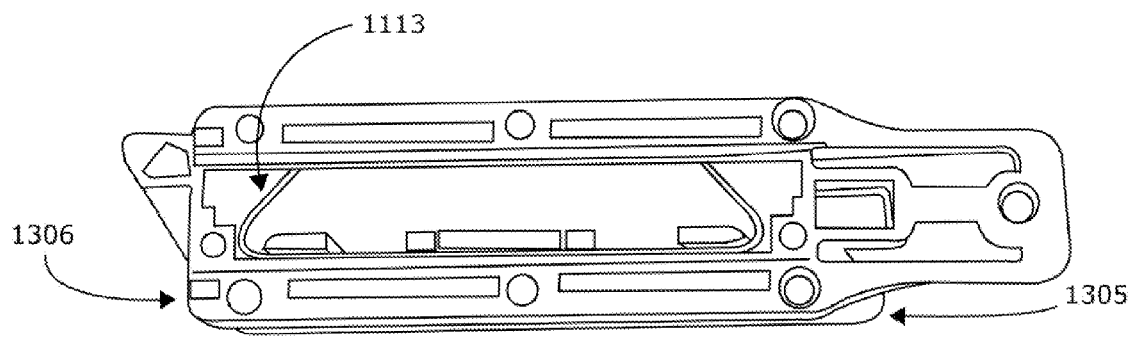
FIG. 13B shows an underside view of a leaf spring of the leaf spring size adjuster according to an embodiment of the present invention of FIG. 13A.
Figure 13C:
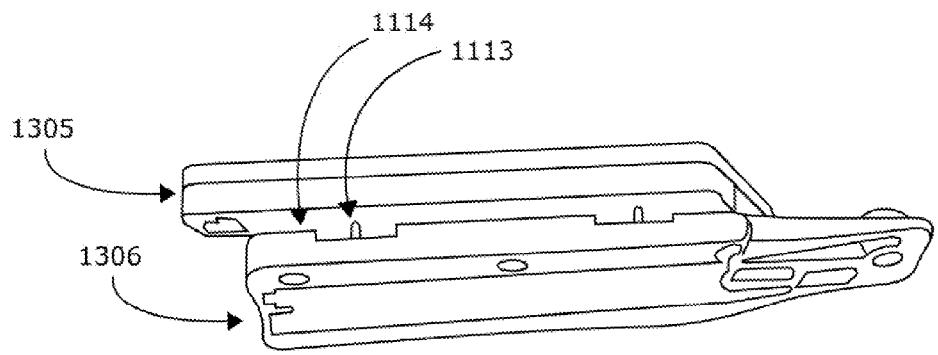
FIG. 13C shows another side view of the leaf spring of the leaf spring size adjuster according to an embodiment of the present invention of FIG. 13B.

In referring now to FIG. 13A shows leaf spring size adjuster 1300 for actuating slider 115 of adjustable curette 180 according to an embodiment of the present invention. FIG. 13B shows leaf spring size adjuster as composed of a front piece 1305 and a back piece 1306. The back piece houses leaf spring 1113. FIG. 13C shows a top view of leaf spring 1113 inside back piece 1306. During use, leaf spring size adjuster 1300 may be advantageous to user for temporarily fixing a user-preferred size of adjustable loop when the tops of leaf spring 1113 are fixed inside notches 1103. User can adjust the size by sliding front piece 1305 toward the distal end or aft against back piece 1306 such that notch 1114 lowers the tips of leaf spring 1113 out of notches 1103 allowing leaf spring size adjuster 1300 to move toward the distal end or aft.

Figure 14A:
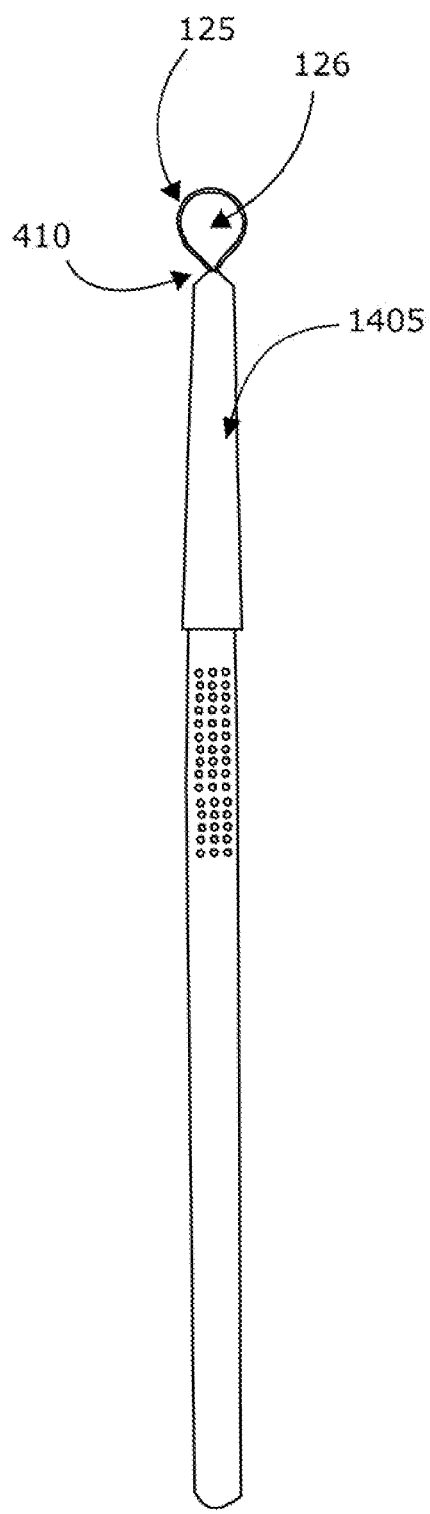
FIG. 14A shows a top-view of the adjustable curette comprising a sleeve for further adjusting the loop area of the adjustable loop according to an alternative embodiment of the present invention.
Figure 14B:
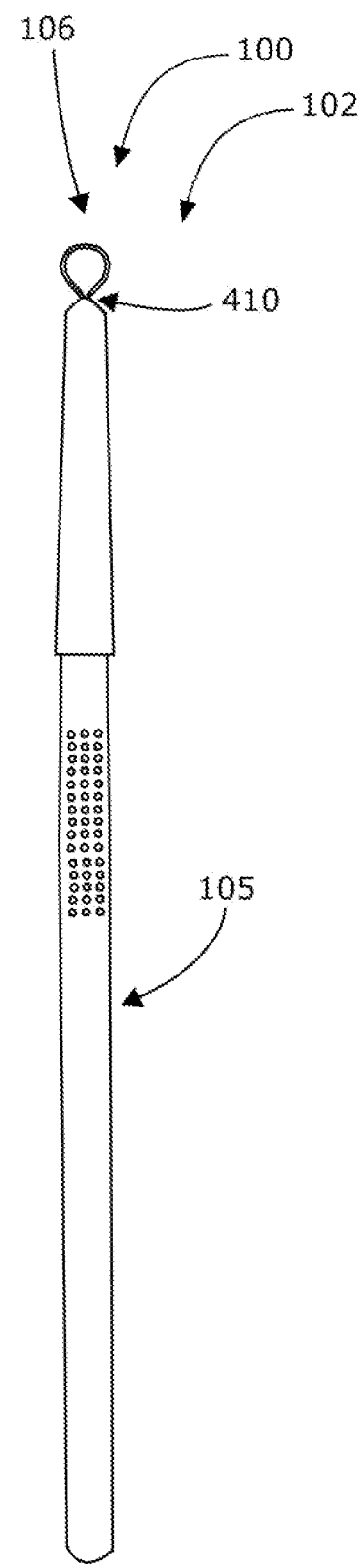
FIG. 14B shows a perspective view of the adjustable curette comprising the sleeve reducing the loop area of the adjustable loop by moving the sleeve upward toward a distal end of the handle according to an alternative embodiment of the present invention of FIG. 14A.

In referring now to FIGS. 14A-B showing an alternative embodiment of adjustable curette 100 comprising handle having triangular profile 102 (although sleeve is not limited to this profile type) and comprising sleeve 1405 for further adjusting loop area 126 of adjustable loop 125 according to an alternative embodiment of the present invention. As shown in FIG. 14A, sleeve 1405 may comprise an elastic or static sleeve that may fit over distal end 106 of handle 105 during non-use. FIG. 14B shows a perspective view of adjustable curette 100 comprising sleeve 1405 useful for reducing loop area 126 of adjustable loop 125 by moving sleeve 1405 upward toward distal end 106 of handle 105. In such a manner, user is able to selectively-adjust sleeve 1405 to squeeze adjustable loop 125 of blade as blade egresses blade opening 410. It should be noted and appreciated that sleeve 1405 is best used with handle having triangular profile 102 and single blade opening 410 as opposed to handle having "Y" head profile. The sleeve may also be used in conjunction with a Y head profile. Sleeve may be loosely fit over handle, or may click and set in place for predetermined head sizes.

In an alternative embodiment of the present invention, adjustable curette 100 may comprise a pair of oppositely charged magnets for adjusting loop area 126 of adjustable loop 125. The oppositely charged magnets may be utilized for providing a means to adjust loop area 126 of adjustable loop 125. For example, slider 115 may comprise at least one magnet. Sliding channel 120 may comprise an oppositely charged magnet. In such a manner, slider 115 and the opposite magnets of sliding channel 120 may become magnetically coupled and decoupled for selectively-adjusting a fixed position of adjustable loop 125.

Figure 15:
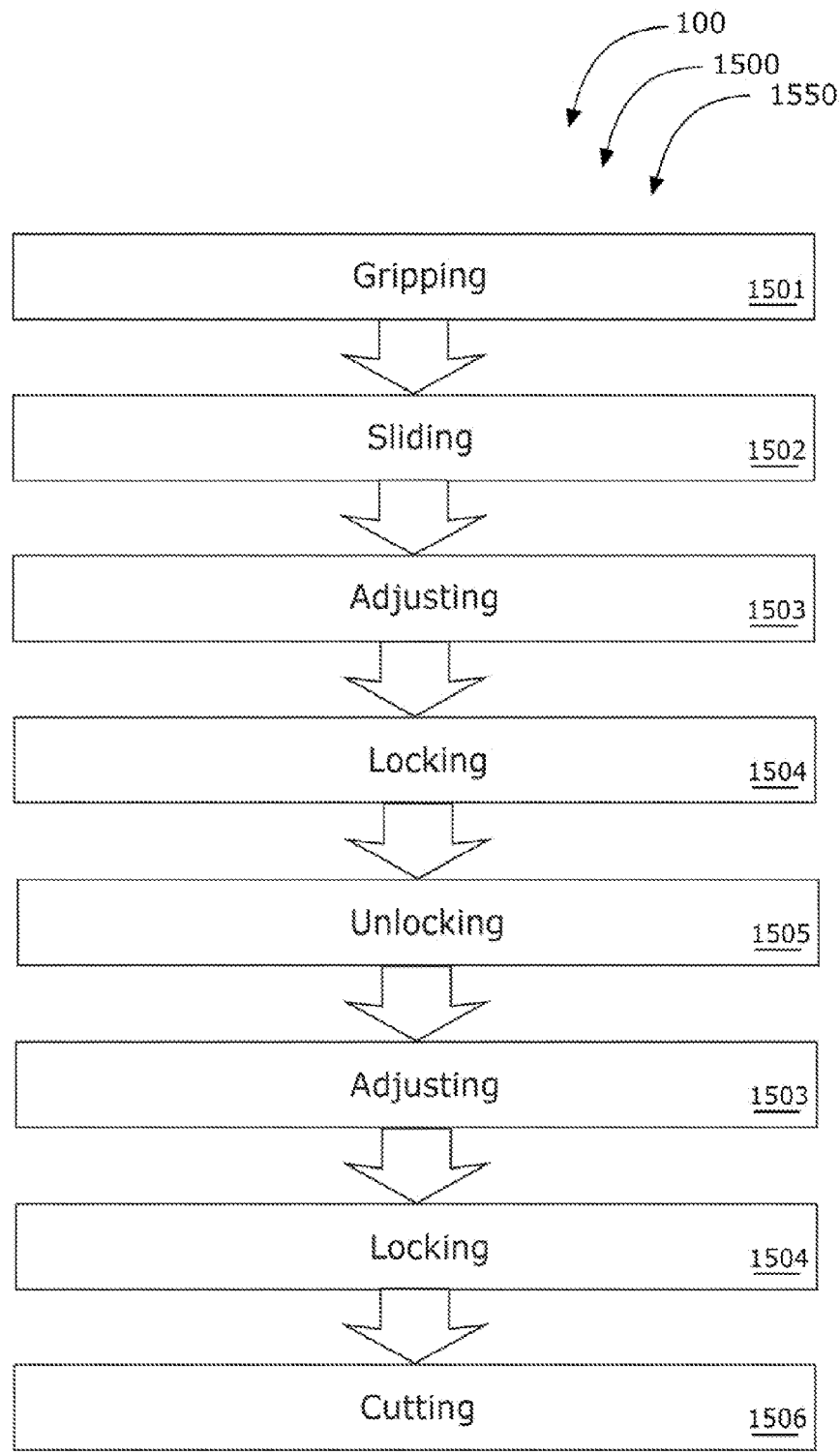
FIG. 15 is a flowchart illustrating a method of use for the adjustable curette according to an embodiment of the present invention of FIGS. 1-14.

In referring now to FIG. 15 showing flowchart 1550 illustrating method of use 1500 for adjustable curette according to an embodiment of the present invention of FIGS. 1-14. As shown, method of use 1500 may comprise the steps of: step one 1501, gripping handle 105 of adjustable curette by a working hand of user; step two 1502, sliding slider of adjustable curette via digit of the working hand of user; step three 1503, adjusting slider to loop area of adjustable loop defined by a user-preferred size; and step four 1504, actuating slider in a locked-position to fix the user-preferred size of adjustable loop. Further, method of use 1500 may comprise optional step live 1505, actuating slider 115 from the locked-position to an unlocked-position readjusting and locking once more for use.

Figure 16A:
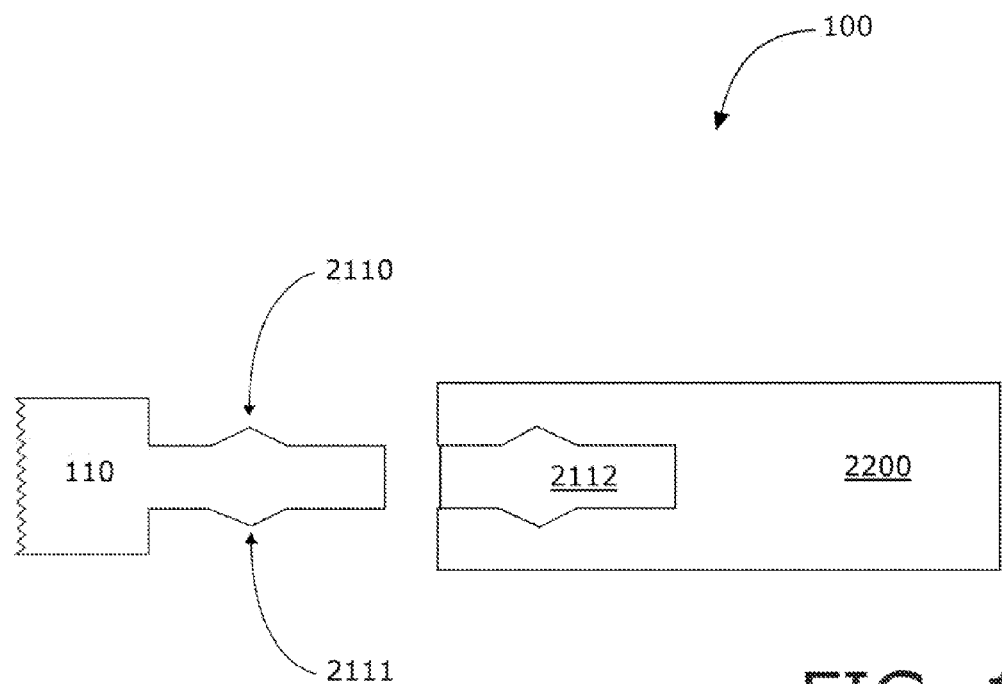
FIG. 16A shows an exploded view of an embodiment of the blade end and blade docking of the present invention.
Figure 16B:
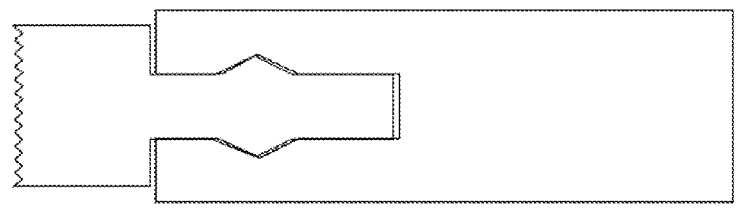
FIG. 16B shows an embodiment of the blade end docking within blade docking of the present invention.

As shown in FIG. 16A, blade 110 may include an extension 2110 at the end of the blade for attachment to the handle and/or slide mechanism. Extension 2110 may include a notch 2111 that can dock within port 2112 of handle portion 2200, as seen in FIG. 16B.

Similarly, as shown in FIG. 17, blade 110 may have extension 2110, with notch 2111, for attachment into slider 115 having complimentary shaped port 2112. Blade may be affixed to slider and/or handle in a multitude of ways comprising mechanical mating, gluing, soldering etc.

Adjustable curette 100 may have a variety of uses. In one manner of use, adjustable curette 100 may serve as an adjustable and lockable disposable dermal curette for performing procedures involving debridements and cutting dead or diseased skin and growths of various sizes. In another manner of use, adjustable curette 100 may be used for ocular procedures. Further, adjustable curette 100 may be used for non-medical use such as pumpkin carving, woodwork, clay pottery, smoothing and finishing, food slicing, shaping, cutting, and for shaving in general, etc.

When applying the curette, with a cautery function, a power lead can be affixed to the fixed end of the blade and a second power lead can be affixed to the slidable end of the blade, thus creating an electrical loop—the blade serving as a resistor. A portion of the blade may be made from a material, of high resistance, while a portion of the blade (particularly towards the slidable end) would, be comprised of a conductive material, (i.e. copper) affixed and integrated with the other material into the blade. This avoids the issue of heating the handle from a portion of the blade that may be within the handle. Alternatively, a large portion of the blade (towards the slidable end) would be insulated with a thin layer of extremely high resistance material to prevent conduction of heat beyond the blade and into the handle.

Power source may be internal, i.e. a battery (with wire lead to slidable end) housed within the handle, preferably the proximal end. As an alternative, an external, power source may be used to include a wired power source. Two leads can attach within the handle to the ends of the blade, the leads resulting in an external port or wire to allow the product to be plugged in (with an optional switch to start power on, the switch preferably being embodied on the tool itself).

Adjustable curette 100 may be manufactured and provided for sale in a wide variety of sizes and shapes for a wide assortment of applications. Upon reading this specification, it should be appreciated that, trader appropriate circumstances, considering such issues as design preference, user preferences, marketing preferences, cost, structural requirements, available materials, technological advances, etc, other kit contents or arrangements such as, for example, including more or less components, customized parts, different color combinations, parts may be sold separately, etc. may be sufficient.

The embodiments of the invention described herein are exemplary and numerous modifications, variations and rearrangements can be readily envisioned to achieve substantially equivalent results, ail of which, are intended to be embraced within the spirit and scope of the invention.

We claim:

1. An adjustable curette comprising:
   a handle, said handle comprising:
      a distal end, and a proximal end, said handle having a longitudinal axis;
      a sliding channel situated along said longitudinal axis; and
      a slider coupled to said sliding channel, said slider movable upwards towards said distal end and downwards towards said proximal end;
   a blade coupled to said handle, said blade comprising:
      a flexible elongated planar member;
      a sharpened cutting edge;
      a first fixed end, said blade first fixed end comprising at least one aperture; and
      a second movable end;
   said handle further comprising;
      a stationary boss adapted to mate with said blade first fixed end at least one aperture so as to fixedly mount said blade first fixed end along said handle distal end; and
      wherein said slider is coupled with said blade second moveable end, said slider adapted to allow said blade second end to move along said longitudinal axis;
      wherein said blade first fixed end and second movable end are coupled to said handle to form a size adjustable loop extending beyond said handle distal end.

2. The adjustable curette of claim 1, wherein said size adjustable loop comprises a loop area defined within said loop, whereby moving said slider along said sliding channel modulates the loop area.

3. The adjustable curette of claim 2 wherein said sliding channel comprises a locking mechanism for fixing a position of said blade second movable end and setting the loop area.

4. The adjustable curette of claim 3 wherein said handle is adapted to be handled by a single band, wherein said locking mechanism comprises a plurality of locking positions along said sliding channel, said locking mechanism adapted to be manipulated by the single hand while holding said handle.

5. The adjustable curette of claim 4 wherein said locking mechanism comprises at least three locking positions, wherein said at least three locking positions are separated by predetermined distances so as to create at least three distinct predetermined loop area sizes.

6. The adjustable curette of claim 5 wherein said locking mechanism comprises at least four locking positions, wherein said at least four locking positions are separated by predetermined distances so as to create at least four distinct predetermined loop area sizes.

7. The adjustable curette of claim 5 wherein at least one of said at least three locking positions creates a first loop area size comprising a diameter less than or equal to 10 mm.

8. The adjustable curette of claim 1 wherein said handle comprises at least three sides arranged with a triangular axial cross-section.

9. The adjustable curette of claim 8 wherein said distal end comprises a blade opening, said blade opening consisting of a single aperture adapted to allow said blade to pass through said blade opening bent over.

10. The adjustable curette of claim 9 wherein said single aperture comprises a slit.

11. The adjustable curette of claim 8 wherein said blade first fixed end defines a plane, and wherein said handle comprises a top side perpendicular to said plane, and a left side, and a right side, and wherein said handle consists of a single sliding channel along said longitudinal axis, said single sliding channel positioned on one of said top side, right side, or left side.

12. The adjustable curette of claim 11 wherein said single channel is arranged down the center of the one of said top side, right side, or left side.

13. The adjustable curette of claim 11 further comprising a gripping surface on a one of said top side, right side, or left side of said handle, said gripping surface distinct from a slider gripping surface.

14. The adjustable curette of claim 11 wherein said sliding channel is positioned on said left side adapted for manipulation of said slider via a right thumb of said user.

15. The adjustable curette of claim 11 wherein said sliding channel is positioned on said top side adapted for manipulation of said slider via an index finger of said user.

16. The adjustable curette of claim 8, wherein said size adjustable loop comprises an area defined within said loop, wherein said slider is structured and arranged to be actuated by a digit of the user to lock said movable end, and thereby fix the loop area.

17. The adjustable curette of claim 16 wherein said slider is structured and arranged to be actuated by a digit of said user to unlock said movable end and adjust said loop area.

18. The adjustable curette of claim 1, wherein said size adjustable loop comprises an area defined within said loop wherein said slider comprises a wheel, wherein rotation of said wheel forces said second blade end along said longitudinal axis and adjusts said loop area.

19. The adjustable curette of claim 1 wherein said distal end comprises a guide having two distinct apertures:
   a first aperture adapted to set an angle of said blade first fixed end emanating from said handle guide relative to said longitudinal axis, and a second aperture adapted to control the angle at which said blade second movable end orients relative to the said longitudinal axis.

20. The adjustable curette of claim 1, wherein said blade comprises a metal.

21. The adjustable curette of claim 20, wherein said blade comprises a shape-memory alloy.

22. An adjustable curette comprising:
   a handle, said handle comprising a distal end, a proximal end, and a longitudinal axis;

a blade comprising a flexible elongated planar member, wherein said blade comprises a cutting edge, and two ends, each of said two ends being fixed in a position along said handle to provide a blade loop, wherein said blade loop extends from said distal end; and a sleeve circumscribing said handle along said distal end positioned around at least a portion of said blade and adapted to constrict said blade loop, said sleeve comprising a distal outlet slit whereby said blade loop extends from said distal end through said sleeve distal outlet slit to define a blade loop area beyond said distal end of said handle;

whereby sliding said sleeve along a longitudinal axis of said handle causes modulation of a diameter of said blade loop area.

23. The adjustable curette of claim 22 wherein said handle comprises at least three sides arranged with a triangular axial cross-section.

24. An adjustable curette handle adapted to be handled by a user's single hand comprising:

a distal end, and a proximal end, said handle having a longitudinal axis;

a sliding channel formed within said handle along said longitudinal axis further comprising a slider, wherein said slider is movable upwards towards said distal end and downwards towards said proximal end within said sliding channel;

a blade comprising a flexible elongated planar member with a sharpened edge, said blade comprising two ends, whereby said blade is folded over to couple said two ends to form a mated end and a blade loop; and wherein said slider fixedly coupled to said blade two ends mated end via a securer;

wherein said distal end comprising a blade opening comprising a single slit adapted to allow folded blade to pass through;

wherein said sliding channel comprises a locking mechanism to lock a position of said slider relative to said sliding channel and to set a loop area of said blade loop;

wherein said locking mechanism comprises a plurality of locking positions along said sliding channel, wherein at least one of said plurality locking positions creates a first loop area size comprising a diameter less than or equal to 10 mm;

wherein said locking mechanism adapted to be manipulated by the user's single hand while handling said handle; and whereby moving said slider along said sliding channel modulates a diameter of said blade loop area.

25. The adjustable curette handle of claim 24 wherein said handle comprises three sides arranged with a triangular axial cross-section.

26. The adjustable curette handle of claim 25 wherein said three sides comprise a first side comprising said sliding channel, a second side, and a third side, wherein said second and third side each comprise a flat surface devoid of a sliding channel.

* * * * *